United States Patent [19]

Mao et al.

[11] 4,178,382

[45] Dec. 11, 1979

[54] N-SUBSTITUTED TRIORGANOSTANNYLHYDRO-CARBYL-CARBOXYLIC ACID HYDRAZIDES

[75] Inventors: Chung-Ling Mao, Sandy Hook; Richard J. Strunk, Cheshire; Winchester L. Hubbard, Woodbridge, all of Conn.

[73] Assignee: Uniroyal, Inc., New York, N.Y.

[21] Appl. No.: 917,143

[22] Filed: Jun. 19, 1978

[51] Int. Cl.$^2$ .......................... C01B 6/13; C01B 6/22; C01B 35/00

[52] U.S. Cl. ........................................ 424/288; 544/4; 546/4; 260/345.7 R; 260/340.5 R; 260/345.8 R; 260/347.2; 260/347.4; 71/97; 260/326.14 R; 260/326.22; 260/333; 260/347.3; 260/429.7; 424/247; 424/248.4; 424/263; 424/267; 424/274; 424/283; 424/285; 544/64

[58] Field of Search .......... 260/429.7, 345.7, 346.1 M, 260/347.3, 326.22, 293.86, 333, 326.14 R, 295 H; 544/58, 64; 424/267, 274, 263, 248.4, 285, 283, 247, 288; 71/97

[56] References Cited

U.S. PATENT DOCUMENTS

| | | | |
|---|---|---|---|
| 3,440,255 | 4/1969 | Matsuda et al. | 260/429.7 |
| 3,520,910 | 7/1970 | Lengnick et al. | 260/429.7 |
| 3,538,088 | 11/1970 | Hartmann | 260/429.7 X |
| 3,723,089 | 3/1973 | Peterson | 260/429.7 X |
| 3,725,446 | 4/1973 | Peterson | 260/429.7 |
| 3,784,580 | 1/1974 | Peterson | 260/429.7 |
| 3,850,970 | 11/1974 | Peterson | 260/429.7 |
| 3,864,371 | 2/1975 | Inman et al. | 260/439 R |
| 3,976,672 | 8/1976 | Strunk et al. | 260/429.7 |
| 4,026,934 | 5/1977 | Daum et al. | 544/64 X |

FOREIGN PATENT DOCUMENTS

| | | | |
|---|---|---|---|
| 2554790 | 7/1976 | Fed. Rep. of Germany | 260/429.7 |
| 2558163 | 7/1976 | Fed. Rep. of Germany | 260/429.7 |

*Primary Examiner*—Helen M. S. Sneed
*Attorney, Agent, or Firm*—Paul H. Ginsburg

[57] ABSTRACT

Disclosed are N-substituted triorganostannylhydrocarbylcarboxylic acid hydrazides useful as insecticides.

21 Claims, No Drawings

N-SUBSTITUTED TRIORGANOSTANNYLHYDRO-CARBYLCARBOXYLIC ACID HYDRAZIDES

BACKGROUND OF THE INVENTION

The present invention relates to N-substituted triorganostannylhydrocarbylcarboxylic acid hydrazides useful as insecticides.

Various substituted organotin compounds are known to be useful as pesticides, acaricides, bactericides, fungicides, herbicides or protective coatings.

U.S. Pat. No. 3,976,672 discloses (hydrocarbylphenylsulfonyl)alkyltrimethylstannanes. Although these compounds exhibit insecticidal properties they are generally too phytotoxic to be used on a crop such as cotton.

U.S. Pat. No. 3,538,088 relates to preparations for combatting molluscs (snails, insect larvae) containing as active substance a compound of the general formula $(R_1)(R_2)(R_3)SnX_1CX_2YNR_4R_5$, wherein $R_1$, $R_2$ and $R_3$ are phenyl or substituted phenyl, and $X_1$ and $X_2$ are sulfur and/or oxygen.

U.S. Pat. No. 3,520,910 discloses organosubstituted tin aminocarbamates of the formula $(R)_2R'SnNRCOONX$ useful as catalysts for curing silicone rubbers and preparing urethane foams.

German Patent Publications Nos. 2,558,163 and 2,554,790 disclose tetrasubstituted tin compounds of the formula $(CH_3)_3Sn(CH_2)_nCR'H-X$ as herbicides and pesticides. One of those compounds is $(CH_3)_3SnCH_2CH_2CONHNH_2$, 3-trimethylstannylpropionic acid hydrazide, which is the starting compound for the synthesis of many of the compounds of the present invention. It appears as Compound 148 in Table I below. Compound 148 and many compounds of the present invention may also be named as derivatives of propanoic acid rather than of propionic acid. In naming many compounds of the present invention, a comma is often inserted between the words "acid" and "hydrazide".

The compounds of the present invention possess unusually good insecticidal properties, especially against the order Lepidoptera. The larval stages of *Heliothis virescens* (tobacco budworm) and *Heliothis zea* (cotton bollworm) cause considerable damage to cotton. The compounds of this invention are distinguished from prior art organotin compounds proposed for insect control because they exhibit high efficacy at low rates of application, with little or no phytotoxicity.

SUMMARY OF THE INVENTION

The present invention relates to a compound having the formula $R_3SnACONR^1X$, wherein R is $C_1$–$C_4$ alkyl, $C_3$–$C_6$ cycloalkyl, or $C_6$–$C_{10}$ aryl; A is $C_1$–$C_5$ alkylene or $C_8$ aralkylene; $R^1$ is hydrogen, $C_1$–$C_{12}$ alkyl, $C_7$–$C_9$ aralkyl, $C_2$–$C_{12}$ alkanoyl, $C_7$–$C_{11}$ aroyl, or $C_1$–$C_{12}$ alkyl substituted with hydroxy, cyano, $C_1$–$C_{14}$ alkoxycarbonyl, $C_1$–$C_4$ alkylsulfonyl, $C_6$–$C_{10}$ arylsulfonyl, $C_1$–$C_4$ alkanoyl, $C_6$–$C_{10}$ aroyl, or $C_5$–$C_6$ 2-hydroxycycloalkyl; and X is $-NR^2R^3$, $-N=CR^4R^5$, $-NR^6COR^7$, or $-NR^8CYNR^9R^{10}$, wherein Y is divalent oxygen or sulfur; $R^2$ and $R^3$ may be the same or different and are hydrogen, provided that one of $R^2$ and $R^3$ is other than hydrogen, or are 2-hydroxycyclohexyl, substituted or unsubstituted $C_1$–$C_{17}$ alkyl, substituents being the same or different and being hydroxy, $C_6$–$C_{10}$ aryl, $C_1$–$C_4$ alkoxy, $C_7$–$C_{11}$ alkoxyaryloxy, tetrahydropyranyloxy, phenylsulfonylethyl, phenyl substituted with halogen, $C_1$–$C_{18}$ alkyl, $C_6$–$C_{10}$ aryl, $C_1$–$C_4$ alkoxy, or phenoxy, or are $R^{11}OOCNR^{12}R^{13}$, wherein $R^{11}$ is $C_3$–$C_6$ cycloalkylene or substituted or unsubstituted $C_2$–$C_{12}$ alkylene, the substituents being the same or different and being $C_6$–$C_{10}$ aryl, $C_1$–$C_4$ alkoxy, $C_7$–$C_{11}$ alkoxyaryloxy, or tetrahydropyranyloxy; $R^{12}$ is $C_1$–$C_{18}$ alkyl, $C_3$–$C_{10}$ cycloalkyl, $C_6$–$C_{10}$ aryl, or phenyl substituted with halogen, $C_1$–$C_8$ alkyl, $C_1$–$C_4$ alkoxy, $C_2$–$C_6$ alkoxycarbonyl, trifluoromethyl, or $C_1$–$C_4$ alkylphenylsulfonyl; and $R^{13}$ has the meanings of $R^1$ above; or $R^2$ and $R^3$ are joined together forming $C_4$–$C_6$ alkylene, $C_4$–$C_6$ oxydialkylene, or methylenebis(aminomethylene)-N,N-bis(2-trymethylstannylethylcarbonylamino); $R^4$ and $R^5$ may be the same or different and are hydrogen, provided that one of $R^4$ and $R^5$ is other than hydrogen, or are $C_1$–$C_{11}$ alkyl, $C_3$–$C_{10}$ cycloalkyl, $C_7$–$C_{12}$ bicycloalkenyl, $C_7$–$C_{11}$ aralkyl, $C_8$–$C_{10}$ arylalkenyl, $C_6$–$C_{10}$ aryl, furyl, pyridyl, indolyl, dihydropyranyl, or phenyl substituted with $C_1$–$C_8$ alkyl, hydroxy, halogen, $C_1$–$C_8$ alkoxy, methylenedioxy, $C_6$–$C_{10}$ aryloxy, benzyloxy, $C_2$–$C_8$ dialkylamino, $C_1$–$C_8$ alkylamino, $C_6$–$C_{12}$ arylamino, cyano, or nitro, or $R^4$ and $R^5$ are joined together forming $C_2$–$C_5$ alkylene; $R^6$, $R^8$ and $R^{10}$ may be the same or different and have the meanings of $R^1$ above; $R^7$ is $C_1$–$C_{17}$ alkyl, $C_3$–$C_{10}$ cycloalkyl, $C_6$–$C_{10}$ aryl, $C_8$–$C_{10}$ aralkenyl, furyl, phenothiazin-10-yl, trimethylstannylethyl, or phenyl substituted with halogen, $C_1$–$C_4$ alkyl, $C_6$–$C_{10}$ aryl, $C_1$–$C_4$ alkoxy, phenylazo, carboxy, nitro, alkali metal carboxy, or $C_2$–$C_{12}$ alkoxycarbonyl, or $R^7$ is a pyridylenebis(carbonylamino) group connecting two $R_3SnACONR^1-$groups, wherein R, A, and $R^1$ are as defined above; $R^9$ is $C_1$–$C_{18}$ alkyl, $C_3$–$C_5$ alkenyl, $C_3$–$C_{10}$ cycloalkyl, $C_6$–$C_{10}$ aryl, $C_3$–$C_8$ alkoxycarbonylalkyl, $C_7$–$C_9$ aralkyl, or phenyl substituted with halogen, $C_1$–$C_{12}$ alkyl, $C_1$–$C_4$ alkoxy, nitro, cyano, trifluoromethyl, or alkali metal sulfo. The terms alkyl and alkylene comprise linear and branched moieties, and the term cycloalkyl includes bridged and non-bridged groups.

The present invention also relates to a method of controlling insects on plants comprising treating a plant with an insecticidally effective amount of a compound of the formula $R_3SnACONR^1X$ above, and to compositions comprising insecticidally effective amounts of compounds of said formula, together with a diluent or carrier.

The present invention also relates to a method of preparing compounds of the formula $R_3SnACONR^1X$ wherein R, A, $R^1$ and X are as defined above by reaction of a compound of the formula $R_3SnACONHNH_2$ (hereinafter referred to as compound (I)) with a compound of the formula $R^5CHO$, $R^4R^5CO$, $R^9N=C=Y$, $R^7COZ$, $R^7COOR^{14}$, $(R^7CO-)_2O$,

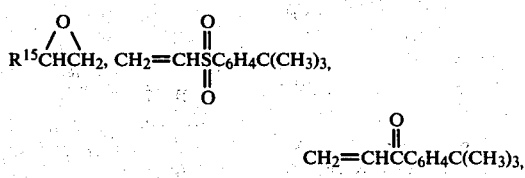

$CH_2=CR^{14}COOR^{16}$, $CH_2=CR^{14}CN$, or $R^{17}Z$, or by heating compound (I), wherein R, A, $R^1$, X, Y, $R^4$, $R^5$, $R^9$ and $R^7$ are as defined above; $R^{14}$ and $R^{16}$ may be the same or different and are hydrogen, $C_1$–$C_{12}$ alkyl or $C_6$–$C_{10}$ aryl; $R^{15}$ is hydrogen $C_6$–$C_{10}$ aryl, $C_3$–$C_6$ cycloalkylene or substituted or unsubstituted $C_1$–$C_{17}$ alkyl, the substituents being $C_1$–$C_4$ alkoxyaryloxy, $C_7$–$C_{11}$ alkoxyaryloxy, $C_6$–$C_{10}$ aryl or tetrahydropyranoyloxy; $R^{17}$ is $C_1$–$C_{18}$ alkyl, $C_7$–$C_{10}$ aralkyl or $C_7$–$C_{10}$ cycloalkyl; and Z is halogen such as fluorine, chlorine, bromine, or iodine.

DESCRIPTION OF THE PREFERRED EMBODIMENTS

Compounds of the present invention, wherein $R^1$ is hydrogen, and X is $-N=CR^4R^5$, wherein $R^4$ is hydrogen, and $R^5$ is as defined above, may be obtained by reaction of compound (I) with an aldehyde of the formula $R^5CHO$ as follows:

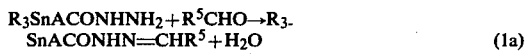
$$R_3SnACONHNH_2 + R^5CHO \rightarrow R_3SnACONHN=CHR^5 + H_2O \quad (1a)$$

Compounds of the present invention wherein $R^1$ is hydrogen, and X is $-N=CR^4R^5$, wherein $R^4$ is other than hydrogen, may be obtained by reaction of compound I with a ketone of the formula $R^4R^5CO$ as follows:

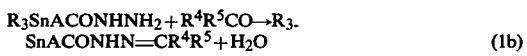
$$R_3SnACONHNH_2 + R^4R^5CO \rightarrow R_3SnACONHN=CR^4R^5 + H_2O \quad (1b)$$

In reactions (1a) and (1b), the temperature should be 0°–100° C., preferably 20°–80° C., the pressure should preferably be 1–2 atmospheres, more preferably ambient pressure (of about one atmosphere as found in the usual laboratory) the molar ratio of the aldehyde or ketone to compound (I) should initially range from an equimolar ratio to a tenfold excess of the aldehyde or ketone, and more preferably there should be a 5–10 mole % excess of aldehyde or ketone over compound (I). Examples of solvents that may be used for reactions (1a) and (1b) are $C_1$–$C_4$ alcohols, mixtures of $C_1$–$C_4$ alcohols and water containing up to 50 volume % of water, ethers such as diethyl ether and tetrahydrofuran, aromatic hydrocarbons such as toluene, or an excess of the reactant aldehyde or ketone may be used as the solvent. The preferred solvents are $C_1$–$C_4$ alcohols and aqueous mixtures thereof.

Compounds of the present invention, wherein $R^1$ is hydrogen, and X is $-NR^8CYNR^9R^{10}$, wherein $R^8$ and $R^{10}$ are hydrogen, and Y and $R^9$ are as defined above, may be prepared in high yields by the following reaction of organic isocyanates or thiocyanates, wherein Y is divalent oxygen or divalent sulfur respectively, with compound I in an aprotic solvent:

$$R_3SnACONHNH_2 + R^9N=C=Y \rightarrow R_3SnACONHNHCYNHR^9 \quad (2)$$

When Y is oxygen, the temperature of reaction (2) should be 0°–100° C., preferably 10°–60° C. When Y is sulfur, the temperature of reaction (2) should be 20°–120° C., preferably 60°–80° C. The pressure of reaction (2) should preferably be ambient pressure or greater, preferably ambient pressure. When Y is oxygen the initial molar ratio of one reactant to another should preferably be 1 to 1. When Y is sulfur, the initial molar ratio of one reactant to another should preferably be 1 to 1 with a slight excess of $R^9N=C=S$. Any inert aprotic solvent, such as an ether, a hydrocarbon, tetrahydrofuran or benzene may be used in reaction (2). When Y is sulfur, a $C_1$–$C_6$ alcohol may also be used as the solvent. The product of reaction (2) is usually recrystallized from aqueous alcohol solution, a solution of a $C_1$–$C_6$ alcohol being preferred. When Y is sulfur, the product may also be recrystallized from a hydrocarbon solvent.

Compound (I) may also be reacted with an acyl halide of the formula $R^7COZ$, wherein $R^7$ is as defined above and wherein Z is halogen (e.g. fluorine, chlorine, bromine, or iodine), in an aprotic medium and in the presence of a hydrogen halide acceptor, a base B, to yield a compound of the present invention wherein $R^1$ is hydrogen and X is $-NR^6COR^7$, wherein $R^6$ is hydrogen, as follows:

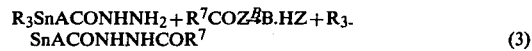
$$R_3SnACONHNH_2 + R^7COZ \xrightarrow{B} B.HZ + R_3SnACONHNHCOR^7 \quad (3)$$

In reaction (3), the temperature should be 0°–100° C., preferably 0°–50° C., the pressure should preferably be ambient pressure, and the initial molar ratio of one reactant to another should preferably be 1 to 1. Any inert aprotic solvent, such as a $C_2$–$C_{10}$ ether or a $C_6$–$C_{10}$ hydrocarbon, may be used. The hydrogen halide acceptor B, should preferably be a base such as trialkylamine (for example, triethylamine). The products isolated from reaction (3) are preferably purified by recrystallization from hydrocarbons or from aqueous solutions of $C_1$–$C_6$ alcohols.

A compound of the present invention of the formula $R_3SnACONHNHCOR^7$ may also be prepared from esters of the formula $R^7COOR^{14}$, wherein $R^{14}$ is a $C_1$–$C_4$ alkyl, and anhydrides of carboxylic acids as shown in reactions (4) and (5) respectively:

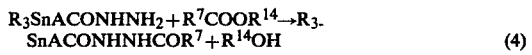
$$R_3SnACONHNH_2 + R^7COOR^{14} \rightarrow R_3SnACONHNHCOR^7 + R^{14}OH \quad (4)$$

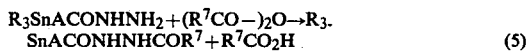
$$R_3SnACONHNH_2 + (R^7CO-)_2O \rightarrow R_3SnACONHNHCOR^7 + R^7CO_2H \quad (5)$$

In reaction (4), the temperature should be 0°–150° C., preferably 60°–100° C., the pressure should preferably be ambient pressure, and the initial molar ratio of one reactant to another should preferably be equimolar to a slight excess of ester. The solvents that may be used include $C_1$–$C_4$ aliphatic alcohols and mixtures of such alcohols with water containing up to 50% by volume of water. The preferred solvents are $C_1$–$C_4$ aliphatic alcohols.

In reaction (5), the temperature should be 0°–100° C., preferably 20°–80° C., the pressure should be 1–2 atmospheres, preferably ambient pressure, and the initial molar ratio of one reactant to another should preferably range from equimolar to a slight excess of anhydride. Aprotic solvents such as ethers (for example, tetrahydrofuran), aromatic hydrocarbons such as toluene, and polar solvents such as acetonitrile and dimethylformamide may be used. The preferred solvents for reaction (5) are ethers and aromatic hydrocarbons.

Compounds of the present invention wherein $R^1$ is hydrogen, and X is $-NR^2R^3$, wherein $R^2$ is hydrogen and $R^3$ is, for instance, hydroxycyclohexyl or $-CH_2CHR^{15}OH$, wherein $R^{15}$ is hydrogen, $C_6$–$C_{10}$ aryl, $C_3$–$C_6$ cycloalkylene or substituted or unsubstituted $C_1$–$C_{17}$ alkyl, the substituents being $C_7$–$C_{11}$ alkoxyaryloxy, tetrahydropyranyloxy, or $C_6$–$C_{10}$ aryl, may be prepared by reacting compound (I) with one equivalent of an organic epoxide as follows:

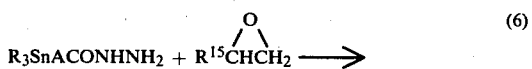
$$R_3SnACONHNH_2 + R^{15}CH\overset{O}{\underset{}{\diagdown\!\!\diagup}}CH_2 \longrightarrow \quad (6)$$

-continued
$$R_3SnACONHNHCH_2CHR^{15}OH$$

In reaction (6), the temperature should be 20°–100° C., preferably 40°–80° C., the pressure should preferably be 1–10 atmospheres, more preferably 2 atmospheres, and the initial molar ratio of the reactants should preferably range from equimolar to a slight excess of compound (I) and should more preferably be equimolar. The preferred solvents for reaction (6) are $C_1$–$C_4$ alcohols or aqueous solutions of $C_1$–$C_4$ alcohols containing up to 50% by volume water. The more preferred solvents are $C_1$–$C_4$ alcohols.

Compounds of the present invention wherein $R^1$ is hydrogen, and X is —$NR^2R^3$, wherein $R^2$ and $R^3$ are each —$CH_2CHR^{15}OH$, wherein $R^{15}$ is as defined for reaction (6), may be prepared by reacting compound I with two equivalents of an organic epoxide as follows:

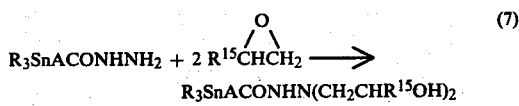
(7)

In reaction (7), the temperature should be 0°–100° C., preferably 20°–80° C., and the pressure should preferably be 1–10 atmospheres. When a high temperature is employed, a closed system is preferred in order to prevent the loss of epoxides such as ethylene oxide. The initial molar ratio of compound (I) to epoxide in reaction (7) is preferably 1 to 2 and the more preferred ratio is 1 to 4, the excess epoxides being recovered after the reaction. A large excess of epoxide may also be used. Any inert solvent such as water, $C_1$–$C_6$ alcohols, and $C_1$–$C_6$ alcohol-water mixtures may be used for reaction (7). The products isolated in reaction (7) may be purified by vacuum distillation or by recrystallization from a suitable solvent such as a $C_1$–$C_6$ alcohol.

The products of reaction (6) possess reactive protons and react with one equivalent of an organic isocyanate to yield compounds wherein $R^1$, $R^3$ and $R^{15}$ remain the same and wherein $R^2$ is —$CONHR^9$, wherein $R^9$ has the same meanings as $R^9$ in reaction (2) and Y is divalent oxygen or divalent sulfur, as follows:

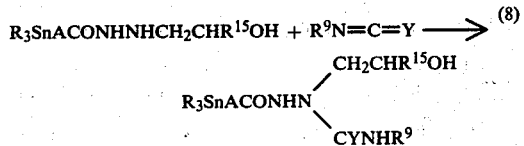
(8)

In reaction (8), the temperature should be 0°–30° C., preferably 10°–20° C., the pressure should preferably be 1–2 atmospheres, more preferably ambient pressure, and the initial molar ratio of one reactant to another is preferably 1 to 1. The solvent used for reaction (8) should be an aprotic solvent. Examples of such solvents are acetonitrile, dimethyl formamide, aromatic hydrocarbons such as toluene, and ethers such as tetrahydrofuran and diethyl ether. A preferred solvent is diethyl ether.

The products of reaction (7) possess reactive protons and react with two equivalents of an organic isocyanate to yield compounds wherein $R^1$ and $R^{15}$ remain the same and wherein $R^2$ and $R^3$ are each

wherein $R^9$ has the same meanings as $R^9$ in reaction (2), and Y is divalent oxygen as follows:

$$R_3SnACONH(CH_2CHR^{15}OH)_2 + 2R^9N=C=Y \rightarrow R_3SnACONH(CH_2CHR^{15}OYCNHR^9)_2 \quad (9)$$

In reaction (9), the reaction temperature should be 0°–120° C., preferably 60°–80° C., the pressure should preferably be at least one atmosphere, and the initial molar ratio of the product of reaction (7) to the organic isocyanate should preferably be 1 to 2. Any inert aprotic solvent such as an ether, a hydrocarbon, tetrahydrofuran or benzene may be used.

The products of reaction (7) undergo a cyclodehydration reaction on heating yielding a compound wherein $R^1$ and $R^{15}$ remain the same but $R^2$ and $R^3$ form a substituted oxydialkylene group as follows:

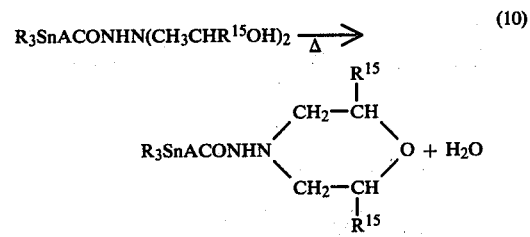
(10)

In reaction (10), the temperature should be 130°–220° C., the pressure should preferably be one atmosphere, and no solvent is required. The reaction product may be purified by vacuum distillation under a pressure of 10–55 Pa at a temperature of 120°–160° C.

Compound (I) can also be made to form adducts of olefin containing such activating groups as cyano, alkanoyl, aroyl, alkoxycarbonyl, aminocarbonyl, sulfonyl, or carboxy. In such products $R^1$ is hydrogen and X is —$NR^2R^3$, wherein $R^2$ is hydrogen and $R^3$ is cyanoethyl, $C_4$–$C_{11}$ alkanoylethyl, $C_9$–$C_{13}$ aroylethyl, phenylsulfonylethyl, $C_4$–$C_{15}$ alkoxycarbonylethyl, $C_4$–$C_{11}$ aminocarbonylethyl or carboxyethyl. Olefins that may be so reacted with compound (I) include acrylonitrile, methyl vinyl ketone, acrolein, phenyl vinyl sulfone, ethyl acrylate, acrylamide, acrylic acid, or acrylic acid salt. When, for example, the activating group is sulfonyl, the following reaction takes place:

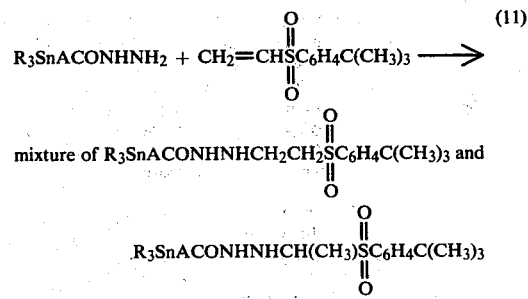
(11)

Examples of a reaction occurring when compound (I) is reacted with an olefin containing cyano or alkoxycarbonyl groups are the following:

$$R_3SNACONHNH_2 + CH_2=CHCN \rightarrow R_3\text{-}SnACONHNHCH_2CH_2CN \quad (12)$$

$$R_3SnACONHNH_2 + CH_2=CHCOOR^{16} \rightarrow R_3\text{-}SnACONHNHCH_2CH_2COOR^{16} \quad (13)$$

In reaction (13), $R^{16}$ is $C_1$–$C_{12}$ alkyl. In reactions (11), (12) and (13), the temperature should be 0°–100° C., preferably 40°–75° C., the pressure should preferably be 1–2 atmospheres, more preferably ambient pressure, and the molar ratio of compound (I) to olefin should range from 1 to 1, up to a 5 mole % excess of olefin and should preferably be 1 to 1. Among the solvents usable for reactions (11) and (12) are $C_1$–$C_4$ alcohols and water containing up to 80% by volume of water, or dimethylformamide, and dimethylsulfoxide. Said mixtures of $C_1$–$C_4$ alcohols and water are preferred.

Compound (I) may also be reacted with one or two equivalents of an aliphatic halide of the formula $R^{17}Z$ wherein $R^{17}$ is as defined above and wherein Z is halogen (for example, fluorine, chlorine, bromine or iodine) in an aprotic solvent and in the presence of a hydrogen halide acceptor, a base B, to yield compounds of the present invention wherein $R^1$ is hydrogen and X is respectively $NHR^{17}$ or $N(R^{17})_2$ as follows:

$$R_3SnACONHNH_2 + R^{17}Z \xrightarrow{B} B \cdot HZ + R_3\text{-}SnACONHNHR^{17} \quad (14)$$

$$R_3SnACONHNH_2 + 2R^{17}Z \xrightarrow{2B} 2B \cdot HZ + R_3\text{-}SnACONHN(R^{17})_2 \quad (15)$$

Table I lists various compounds of the present invention that were prepared according to the methods described above, and also lists their physical properties. The column of Table I entitled "Reaction Number" indicates which of the above reactions was used to prepare a particular compound. The preparation of the compounds listed in Table I is more fully described in Examples 1–16 below.

Table I

| Compound No. | Compound Name | Reaction No. | Melting Point °C. (or Boiling °C.*) | Calculated Value % C | H | N | Sn | S | Found Value % C | H | N | Sn | S |
|---|---|---|---|---|---|---|---|---|---|---|---|---|---|
| 1 | 3'-trimethylstannylpropionic acid 1-methylethylidenehydrazide | 1b | 89.5–90.5 | 37.15 | 6.93 | 9.63 | 40.79 | | 36.96 | 6.99 | 9.63 | 40.73 | |
| 2 | 3-trimethylstannylpropionic acid cyclohexylidenehydrazide | 1b | 115–116 | 43.54 | 7.31 | 8.46 | 35.85 | | 43.52 | 7.46 | 8.49 | 36.22 | |
| 3 | 3-trimethylstannylpropionic acid phenylmethylenehydrazide | 1a | 142.5–143.5 | 46.05 | 5.95 | 8.26 | 35.01 | | 46.05 | 5.98 | 8.18 | 35.16 | |
| 4 | 2-methyl-3-trimethylstannyl-propionic acid phenylmethylenehydrazide | 1a | 128.5–130 | 47.63 | 6.28 | 7.94 | 33.62 | | 47.42 | 6.40 | 7.74 | 33.51 | |
| 5 | 3'-trimethylstannylpropionic acid 2-hydroxyphenylmethylenehydrazide | 1a | 112–114.5 | 43.98 | 5.68 | 7.89 | 33.43 | | 42.76 | 6.00 | 7.33 | 32.37 | |
| 6 | 3'-trimethylstannylpropionic acid 4-methoxyphenylmethylenehydrazide | 1a | 119–120.5 | 45.56 | 6.01 | 7.59 | 32.16 | | 45.53 | 6.18 | 7.55 | 32.12 | |
| 7 | 3'-trimethylstannylpropionic acid 3,4-methylenedioxyphenylmethylenehydrazide | 1a | 140–141.5 | 43.90 | 5.26 | 7.31 | 30.99 | | 43.93 | 5.31 | 7.31 | 30.84 | |
| 8 | 3'-trimethylstannylpropionic acid 4-methylphenylmethylenehydrazide | 1a | 115–116 | 47.63 | 6.28 | 7.94 | 33.62 | | 47.43 | 6.33 | 7.94 | 33.46 | |
| 9 | 3'-trimethylstannylpropionic acid 4-chlorophenylmethylenehydrazide | 1a | 134–135 | 41.81 | 5.13 | 7.50 | | | 41.15 | 5.00 | 7.35 | | |
| 10 | 3'-trimethylstannylpropionic acid 3-nitrophenylmethylenehydrazide | 1a | 173.5–174 | 40.66 | 4.99 | 10.94 | 30.91 | | 40.67 | 5.06 | 10.82 | 30.75 | |
| 11 | 3'-trimethylstannylpropionic acid 4-hydroxy-3-methoxyphenylmethylenehydrazide | 1a | 157(dec) | 43.67 | 5.76 | 7.28 | 30.82 | | 44.00 | 5.84 | 7.11 | 30.74 | |
| 12 | 3'-trimethylstannylpropionic acid 4-dimethylaminophenylmethylenehydrazide | 1a | 176–177 | 47.15 | 6.59 | 11.00 | 31.06 | | 46.95 | 6.84 | 11.07 | 30.36 | |
| 13 | 3'-trimethylstannylpropionic acid 1-naphthylmethylenehydrazide | 1a | 133–134 | 52.48 | 5.70 | 7.20 | 30.50 | | 51.80 | 5.74 | 6.94 | 30.61 | |
| 14 | 3'-trimethylstannylpropionic acid (1-phenylethylidene)hydrazide | 1b | 131.5–132.5 | 47.63 | 6.28 | 7.94 | 33.62 | | 47.24 | 6.42 | 7.97 | 33.57 | |
| 15 | 3-trimethylstannylpropionic acid n-undecylmethylenehydrazide | 1a | 50–52 | 51.82 | 9.18 | 6.72 | 28.45 | | 51.81 | 9.41 | 6.47 | 28.43 | |
| 16 | 3'-trimethylstannylpropionic acid (3-phenyl-2-propenylidene)hydrazide | 1a | 115–116 | 49.35 | 6.07 | 7.67 | 32.51 | | 49.15 | 6.08 | 7.53 | 32.58 | |
| 17 | 3'-trimethylstannylpropionic acid 4-fluorophenylmethylenehydrazide | 1a | 140–141 | 43.73 | 5.36 | 7.85 | | | 43.47 | 5.28 | 7.88 | | |
| 18 | 3'-trimethylstannylpropionic acid 2,6-dichlorophenylmethylenehydrazide | 1a | 118.6–119.6 | 38.28 | 4.45 | 6.87 | | | 37.66 | 4.55 | 6.88 | | |
| 19 | 3'-trimethylstannylpropionic acid 3,4-dichlorophenylmethylenehydrazide | 1a | 140.8–142.3 | 38.28 | 4.45 | 6.87 | | | 37.70 | 4.68 | 6.77 | | |
| 20 | 3'-trimethylstannylpropionic acid (2-furyl)methylenehydrazide | 1a | 148–149 | 40.16 | 5.51 | 8.52 | 36.08 | | 39.62 | 5.58 | 8.59 | 35.17 | |
| 21 | 3'-trimethylstannylpropionic acid 4-cyanophenylmethylenehydrazide | 1a | 188.5– | 46.19 | 5.26 | 11.54 | 32.61 | | 46.16 | 5.14 | 11.24 | 32.47 | |

Table I-continued

| Compound No. | Compound Name | Reaction No. | Melting Point °C. (or Boiling °C.*) | Calculated Value % C | H | N | Sn | S | Found Value % C | H | N | Sn | S |
|---|---|---|---|---|---|---|---|---|---|---|---|---|---|
| | | | 189.5 | | | | | | | | | | |
| 22 | 3'-trimethylstannylpropionic acid (4-acetamidophenyl)methylenehydrazide | 1a | 191–192 | 45.49 | 5.85 | 10.61 | 29.97 | | 45.56 | 5.89 | 10.48 | 29.47 | |
| 23 | 3'-trimethylstannylpropionic acid (1,3-diphenyl-2-propylidene)hydrazide | 1b | 133–134 | 56.91 | 6.37 | 6.32 | 26.78 | | 56.97 | 6.32 | 6.16 | 26.64 | |
| 24 | 3'-trimethylstannylpropionic acid 3,4-dimethoxyphenylmethylenehydrazide | 1a | 158–159.5 | 45.14 | 6.06 | 7.02 | 29.74 | | 45.20 | 6.18 | 7.06 | 29.72 | |
| 25 | 3'-trimethylstannylpropionic acid 2,4-dihydroxyphenylmethylenehydrazide | 1a | 184–185 | 42.08 | 5.43 | 7.55 | 31.99 | | 42.60 | 5.61 | 7.52 | 31.90 | |
| 26 | 3'-trimethylstannylpropionic acid (bicyclo[2.2.1]hept-5-en-2-ylmethylene)hydrazide | 1a | 100.8–103.5 | 47.36 | 6.81 | 7.89 | 33.43 | | 47.14 | 6.70 | 7.82 | 33.22 | |
| 27 | 3'-trimethylstannylpropionic acid (4-benzyloxyphenylmethylene)hydrazide | 1a | 116–117 | 53.96 | 5.89 | 6.29 | 26.66 | | 54.14 | 6.01 | 6.29 | 26.57 | |
| 28 | 3'-trimethylstannylpropionic acid (3,4,5-trimethoxyphenylmethylene)hydrazide | 1a | 179–180 | 44.78 | 6.11 | 6.53 | 27.66 | | 44.52 | 6.19 | 6.47 | 27.51 | |
| 29 | 3'-trimethylstannylpropionic acid (2,5-dimethyl-4-methoxyphenylmethylene)hydrazide | 1a | 132.6–133.6 | 48.39 | 6.60 | 7.05 | 28.89 | | 48.26 | 6.59 | 7.11 | 29.60 | |
| 30 | 3'-trimethylstannylpropionic acid cyclohexylmethylenehydrazide | 1a | 107–109.5 | 45.25 | 7.59 | 8.12 | 34.40 | | 45.16 | 7.94 | 8.19 | 34.36 | |
| 31 | 3'-trimethylstannylpropionic acid [5,6-dihydro-(2,H)-3-pyranylmethylene]hydrazide | 1a | 159.2–160.2 | 41.77 | 6.43 | 8.12 | 34.40 | | 41.26 | 6.52 | 8.03 | 34.27 | |
| 32 | 3'-trimethylstannylpropionic acid (3-pyridylmethylene)hydrazide | 1a | 137–138 | 42.39 | 5.63 | 12.36 | 34.91 | | 42.18 | 5.63 | 12.24 | 34.85 | |
| 33 | 3'-trimethylstannylpropionic acid (3-indolylmethylene)hydrazide | 1a | 206–207 | 47.78 | 5.35 | 11.14 | 31.48 | | 47.90 | 5.59 | 11.30 | 30.81 | |
| 34 | 3'-trimethylstannylpropionic acid (4-n-propoxyphenylmethylene)hydrazide | 1a | 115–116.5 | 48.39 | 6.60 | 7.05 | 29.89 | | 48.37 | 6.77 | 7.00 | 29.65 | |
| 35 | 3'-trimethylstannylpropionic acid (4-n-octyloxyphenylmethylene)hydrazide | 1a | 107–108 | 53.98 | 7.77 | 6.00 | 25.40 | | 53.89 | 7.94 | 5.93 | 25.38 | |
| 36 | 3'-trimethylstannylpropionic acid (4-n-butylphenylmethylene)hydrazide | 1a | 74.5–75.5 | 51.67 | 7.14 | 7.09 | 30.04 | | 52.07 | 7.37 | 6.98 | 30.18 | |
| 37 | 3'-trimethylstannylpropionic acid (4-n-octylphenylmethylene)hydrazide | 1a | 92.5–93.5 | 55.89 | 8.04 | 6.21 | 26.30 | | 55.94 | 8.03 | 6.08 | 26.15 | |
| 38 | 3-trimethylstannyl-2-phenylpropionic acid phenylmethylenehydrazide | 1a | 170–172 | 54.97 | 5.83 | 6.75 | 28.59 | | 55.41 | 5.91 | 7.11 | 27.92 | |
| 39 | 3-methyl-3-trimethylstannylpropionic acid phenylmethylenehydrazide | 1a | 137–139 | 47.63 | 6.28 | 7.94 | 33.62 | | 47.38 | 6.33 | 7.91 | 33.48 | |
| 40 | 3'-methyl-3'-trimethylstannylpropionic acid 2-[(phenylamino)carbonyl]hydrazide | 2 | 152.5–154 | 43.78 | 6.03 | 10.94 | 30.90 | | 43.66 | 6.25 | 10.85 | 30.73 | |
| 41 | 3'-trimethylstannylpropionic acid 2-[(phenylamino)carbonyl]hydrazide | 2 | 145–146 | 42.20 | 5.72 | 11.36 | 32.08 | | 42.20 | 5.74 | 11.33 | 32.18 | |
| 42 | 3'-trimethylstannylpropionic acid 2-[(p-chlorophenylamino)carbonyl]hydrazide | 2 | 176–177 | 38.60 | 4.98 | 10.39 | | | 38.20 | 5.16 | 10.02 | | |
| 43 | 3'-trimethylstannylpropionic acid 2-[(p-methoxyphenylamino)carbonyl]hydrazide | 2 | 141–142 | 42.03 | 5.80 | 10.50 | 29.67 | | 41.88 | 5.85 | 10.36 | 29.62 | |
| 44 | 3'-trimethylstannylpropionic acid 2-[(n-butylamino)carbonyl]hydrazide | 2 | 85–87 | 37.75 | 7.20 | 12.00 | 33.91 | | 37.76 | 7.24 | 12.19 | 33.83 | |
| 45 | 3'-trimethylstannylpropionic acid 2-[(n-octadecylamino)carbonyl]hydrazide | 2 | 78–79 | 54.95 | 9.78 | 7.69 | 21.72 | | 54.94 | 9.91 | 7.69 | 21.62 | |
| 46 | 2'-methyl-3'-trimethylstannylpropionic acid 2-[(phenylamino)carbonyl]hydrazide | 2 | 159.5–160.5 | 43.78 | 6.04 | 10.94 | 30.90 | | 43.08 | 6.02 | 10.86 | 30.17 | |
| 47 | 3'-trimethylstannylpropionic acid 2-[(naphthylamino)carbonyl]hydrazide | 2 | 140–142 | 48.61 | 5.52 | 10.00 | | | 48.42 | 6.14 | 9.87 | | |
| 48 | 3'-trimethylstannylpropionic acid 2-[(m-methylphenylamino)carbonyl]hydrazide | 2 | 125–126 | 43.78 | 6.04 | 10.94 | 30.90 | | 43.72 | 5.97 | 10.89 | 30.34 | |
| 49 | 3'-trimethylstannylpropionic acid 2-[(cyclohexylamino)carbonyl]hydrazide | 2 | 122–123 | 41.52 | 7.24 | 11.17 | 31.56 | | 40.76 | 7.32 | 10.85 | 31.20 | |
| 50 | 3'-trimethylstannylpropionic acid 2-[(o-methoxyphenylamino)carbonyl]hydrazide | 2 | 135–136 | 42.03 | 5.80 | 10.50 | 29.67 | | 41.78 | 5.95 | 10.42 | 29.49 | |
| 51 | 3'-trimethylstannylpropionic acid 2-[(p-fluorophenylamino)carbonyl]hydrazide | 2 | 146–147 | 40.24 | 5.20 | 10.83 | 30.59 | | 39.81 | 5.20 | 10.83 | 29.22 | |
| 52 | 3'-trimethylstannylpropionic acid 2-[(methylamino)carbonyl]hydrazide | 2 | 138–139 | 31.20 | 6.22 | 13.64 | 38.54 | | 30.94 | 6.20 | 13.56 | 38.28 | |
| 53 | 3'-trimethylstannylpropionic acid 2-[(m- | | | | | | | | | | | | |

Table I-continued

| Compound No. | Compound Name | Reaction No. | Melting Point °C. (or Boiling °C.*) | Calculated Value % C | H | N | Sn | S | Found Value % C | H | N | Sn | S |
|---|---|---|---|---|---|---|---|---|---|---|---|---|---|
| | trifluoromethylphenylamino)carbonyl]hydrazide | 2 | 138–139 | 38.39 | 4.60 | 9.59 | | | 38.31 | 4.70 | 9.18 | | |
| 54 | 3'-trimethylstannylpropionic acid 2-[(p-nitrophenylamino)carbonyl]hydrazide | 2 | 195–196 | 123 | 4.86 | 13.50 | 28.60 | | 37.38 | 4.85 | 13.23 | 28.46 | |
| 55 | 3'-trimethylstannylpropionic acid 2-[(2,5-dimethylphenylamino)carbonyl]hydrazide | 2 | 143–144 | 45.26 | 6.33 | 10.56 | 29.81 | | 45.00 | 6.23 | 10.09 | 30.10 | |
| 56 | 3'-trimethylstannylpropionic acid 2-[(2,5-dichlorophenylamino)carbonyl]hydrazide | 2 | 152–153 | 35.57 | 4.36 | 9.57 | 27.04 | | 34.81 | 4.33 | 9.24 | 26.39 | |
| 57 | 3'-trimethylstannylpropionic acid 2-[(3-chlorophenylamino)carbonyl]hydrazide | 2 | 142–143 | 38.60 | 4.98 | 10.39 | 19.34 | | 37.71 | 5.08 | 10.04 | | |
| 58 | 3'-trimethylstannylpropionic acid 2-[(2-fluorophenylamino)carbonyl]hydrazide | 2 | 137–138 | 40.24 | 5.20 | 10.83 | | | 40.06 | 5.27 | 10.81 | | |
| 59 | 3'-trimethylstannylpropionic acid 2-[(phenylamino)thioxomethyl]hydrazide | 2 | 155.5–156.5 | 40.44 | 5.48 | 10.88 | 30.74 | 8.30 | 40.44 | 5.56 | 10.91 | 31.03 | 8.38 |
| 60 | 2'-methyl-3'-trimethylstannylpropionic acid 2-[(butylamino)thioxomethyl]hydrazide | 2 | 118–120 | 37.92 | 7.16 | 11.05 | 31.22 | 8.43 | 37.98 | 7.02 | 10.91 | 31.10 | 8.69 |
| 61 | 2'-methyl-3'-trimethylstannylpropionic acid 2-[(phenylamino)thioxomethyl]hydrazide | 2 | 131–132 | 42.03 | 5.79 | 10.50 | 29.66 | 8.01 | 41.77 | 5.76 | 10.40 | 29.66 | 8.21 |
| 62 | 3'-trimethylstannylpropionic acid 2-[(2-propenylamino)thioxomethyl]hydrazide | 2 | 132.5–133.5 | 34.31 | 6.05 | 12.00 | 33.91 | 9.16 | 33.83 | 6.07 | 11.83 | 33.95 | 8.89 |
| 63 | 3'-trimethylstannylpropionic acid 2-[(methylamino)thioxomethyl]hydrazide | 2 | 159–160 | 29.66 | 5.91 | 12.97 | 36.63 | 9.90 | 29.05 | 5.79 | 12.68 | 36.79 | 9.51 |
| 64 | 3'-trimethylstannylpropionic acid 2-[(4-sulfophenylamino)thioxomethyl]hydrazide, sodium salt | 2 | >250 | 31.99 | 4.13 | 8.61 | | 13.14 | 31.20 | 4.22 | 8.07 | | 13.01 |
| 65 | 3'-trimethylstannylpropionic acid 2-[(1-naphthylamino)thioxomethyl]hydrazide | 2 | 136–137 137 | 46.82 | 5.32 | 9.63 | 27.21 | 7.35 | 46.37 | 5.28 | 9.39 | 27.20 | 7.27 |
| 66 | 3'-trimethylstannylpropionic acid 2-[(cyclohexylamino)thioxomethyl]hydrazide | 2 | 148–149 | 39.82 | 6.94 | 10.72 | 30.27 | 8.17 | 39.29 | 7.07 | 10.76 | 30.11 | 7.99 |
| 67 | 3'-trimethylstannylpropionic acid 2-[(4-fluorophenylamino)thioxomethyl]hydrazide | 2 | 142–143 | 38.64 | 4.99 | 10.40 | | 7.93 | 38.50 | 4.94 | 10.47 | | 8.02 |
| 68 | 3'-trimethylstannylpropionic acid 2-[3-fluorophenylamino)thioxomethyl]hydrazide | 2 | 140–141 | 38.64 | 4.99 | 10.40 | | 7.93 | 37.96 | 4.72 | 10.22 | | 7.84 |
| 69 | 3'-trimethylstannylpropionic acid 2-(cyclopropylcarbonyl)hydrazide | 3 | 110–112 | 37.65 | 6.32 | 8.78 | 37.21 | | 37.67 | 6.36 | 8.88 | 36.96 | |
| 70 | 3'-trimethylstannylpropionic acid 2-acetylhydrazide | 3 | 113–115 | 32.80 | 6.19 | 9.56 | 40.52 | | 32.68 | 7.27 | 9.77 | 40.29 | |
| 71 | 3'-trimethylstannylpropionic acid 2-(n-octadecanoyl)hydrazide | 3 | 94–95 | 55.72 | 9.74 | 5.41 | 22.94 | | 55.77 | 9.74 | 5.43 | 22.64 | |
| 72 | 3'-trimethylstannylpropionic acid 2-(n-hexanoyl)hydrazide | 3 | 66–67 | 41.29 | 7.51 | 8.03 | 34.00 | | 40.89 | 7.51 | 8.07 | 34.47 | |
| 73 | 3'-trimethylstannylpropionic acid 2-(n-propanoyl)hydrazide | 3 | 91–92 | 35.22 | 6.57 | 9.13 | 38.67 | | 35.16 | 6.72 | 9.25 | 38.44 | |
| 74 | 3'-trimethylstannylpropionic acid 2-(2-methylpropanoyl)hydrazide | 3 | 116–118 | 37.42 | 6.91 | 8.73 | 36.98 | | 37.35 | 7.09 | 8.88 | 36.69 | |
| 75 | 3'-trimethylstannylpropionic acid 2-(n-nonanoyl)hydrazide | 3 | 63–65 | 46.06 | 8.25 | 7.16 | 30.35 | | 46.09 | 8.42 | 7.15 | 30.31 | |
| 76 | 3'-trimethylstannylpropionic acid 2-(cyclohexylcarbonyl)hydrazide | 3 | 134–135 | 43.25 | 7.26 | 7.76 | 32.87 | | 42.60 | 7.04 | 7.65 | 32.63 | |
| 77 | 3'-trimethylstannylpropionic acid 2-(n-octanoyl)hydrazide | 3 | 58–59 | 44.59 | 8.02 | 7.45 | 31.47 | | 44.14 | 7.79 | 7.34 | 31.29 | |
| 78 | 3'-trimethylstannylpropionic acid 2-(cinnamoyl)hydrazide | 3 | 128–130 | 47.28 | 5.82 | 7.35 | 31.15 | | 47.44 | 5.95 | 7.34 | 31.04 | |
| 79 | 3'-trimethylstannylpropionic acid 2-(4-methylbenzoyl)hydrazide | 3 | 93–94 | 45.57 | 6.01 | 7.59 | 32.16 | | 45.13 | 6.06 | 7.66 | | |
| 80 | 3'-trimethylstannylpropionic acid 2-(2-methylbenzoyl)hydrazide | 3 | 118–119 | 45.57 | 6.01 | 7.59 | 32.16 | | 45.04 | 6.01 | 7.42 | 32.18 | |
| 81 | 3'-trimethylstannylpropionic acid 2-(3-methylbenzoyl)hydrazide | 3 | 144–145 | 45.57 | 6.01 | 7.59 | 32.16 | | 45.18 | 5.95 | 7.54 | 32.21 | |
| 82 | 3'-trimethylstannylpropionic acid 2-(3,4,5-trimethoxybenzoyl)hydrazide | 3 | 200–201 | 43.18 | 5.89 | 6.29 | 26.67 | | 43.20 | 5.91 | 6.22 | 26.48 | |
| 83 | 3'-trimethylstannylpropionic acid 2-(4-biphenylcarbonyl)hydrazide | 3 | 134–135 | 52.94 | 5.61 | 6.50 | 27.53 | | 52.94 | 5.53 | 6.48 | 27.30 | |
| 84 | 3'-trimethylstannylpropionic acid 2-(4-phenylazobenzoyl)hydrazide | 3 | 160–161 | 49.71 | 5.27 | 12.20 | 25.85 | | 49.66 | 5.20 | 12.19 | 25.60 | |
| 85 | 3'-trimethylstannylpropionic acid 2-(4-t-butylbenzoyl)hydrazide | 3 | 139–140 | 49.54 | 7.09 | 6.80 | 28.80 | | 49.51 | 6.96 | 6.95 | 28.76 | |
| 86 | 3'-trimethylstannylpropionic acid 2-(3,5-dinitrobenzoyl)hydrazide | 3 | 164–165 | 35.09 | 4.08 | 12.59 | | | 34.74 | 4.15 | 12.49 | | |
| 87 | 3'-trimethylstannylpropionic acid | | | | | | | | | | | | |

Table I-continued

| Compound No. | Compound Name | Reaction No. | Melting Point °C. (or Boiling °C.*) | Elemental Analysis Calculated Value % | | | | | Found Value % | | | | |
|---|---|---|---|---|---|---|---|---|---|---|---|---|---|
| | | | | C | H | N | Sn | S | C | H | N | Sn | S |
| | 2-(4-chlorobenzoyl)hydrazide | 3 | 150–151 | 40.09 | 4.92 | 7.19 | | | 40.06 | 4.93 | 7.40 | | |
| 88 | 3'-trimethylstannylpropionic acid 2-(2,4-dichlorobenzoyl)hydrazide | 3 | 129–131 | 36.84 | 4.28 | 6.61 | | | 36.92 | 4.01 | 6.27 | | |
| 89 | 3'-trimethylstannylpropionic acid 2-(benzoyl)hydrazide | 3 | 149–150 | 43.98 | 5.68 | 7.89 | 33.43 | | 43.83 | 5.79 | 7.95 | 33.34 | |
| 90 | 3'-trimethylstannylpropionic acid 2-(n-dodecanoyl)hydrazide | 3 | 78–79 | 49.91 | 8.84 | 6.47 | 27.40 | | 50.01 | 8.96 | 6.50 | 27.27 | |
| 91 | 3'-trimethylstannylpropionic acid 2-(2-furoyl)hydrazide | 3 | 125–126 | 38.30 | 5.26 | 8.12 | 34.41 | | 38.03 | 5.19 | 7.96 | 34.19 | |
| 92 | 2,6-pyridinedicarboxylic acid 2',2"-bis[3'(trimethylstannyl)propanoylhydrazide] | 3 | 223–224 | 36.06 | 5.26 | 11.06 | 37.51 | | 35.57 | 5.31 | 10.98 | 37.15 | |
| 93 | 3'-trimethylstannylpropionic acid 2-[(n-butoxycarbonylmethylamino)carbonyl]hydrazide | 2 | 81–82 | 38.26 | 6.67 | 10.30 | 29.08 | | 38.02 | 6.69 | 10.35 | 28.86 | |
| 94 | 3'-trimethylstannylpropionic acid 2-(phenothiazine-10-carbonyl)hydrazide | 3 | 147–148 | 47.93 | 4.89 | 8.82 | 24.93 | 6.73 | 48.21 | 4.92 | 8.81 | 24.90 | 6.91 |
| 95 | 3'-trimethylstannylpropionic acid 2-(2-carboxybenzoyl)hydrazide | 5 | 115 (dec) | 42.14 | 5.05 | 7.02 | 29.74 | | 42.27 | 5.19 | 6.89 | 29.51 | |
| 96 | 3'-trimethylstannylpropionic acid 2-(2-carboxybenzoyl)hydrazide, sodium salt | | | 39.94 | 4.55 | 6.65 | | | 39.18 | 4.81 | 6.48 | | |
| 97 | 3'-trimethylstannylpropionic acid 2-(3-trimethylstannylpropanoyl)hydrazide | | 103.5–105 | 30.68 | 6.01 | 5.96 | 50.53 | | 30.78 | 6.21 | 6.18 | 50.30 | |
| 98 | 3'-trimethylstannylpropionic acid 2-(2-hydroxy-cyclohexyl)-2-(phenylaminocarbonyl)-hydrazide | 8 | 179.5–180.5 | 48.74 | 6.67 | 8.97 | 25.35 | | 48.46 | 7.04 | 9.04 | 25.37 | |
| 99 | 3'-trimethylstannylpropionic acid 2-(2-hydroxycyclohexyl)hydrazide | 6 | 60–65 | 41.29 | 7.51 | 8.03 | 34.00 | | 41.37 | 7.51 | 7.55 | 32.82 | |
| 100 | 3'-trimethylstannylpropionic acid 2,2-bis[2-(phenylaminocarbonyloxy)ethyl]hydrazide | 9 | waxy solid | 49.94 | 5.94 | 9.70 | | | 49.96 | 6.01 | 10.00 | | |
| 101 | 3'-trimethylstannylpropionic acid 2,2-bis[2-(4-methylphenylsulfonylaminocarbonyloxy)ethyl]hydrazide | 9 | 64–80 (dec) | 42.58 | 5.22 | 7.64 | 16.18 | 8.74 | 41.76 | 5.39 | 7.70 | 16.81 | 8.56 |
| 102 | 3'-trimethylstannylpropionic acid 2,2-bis[2-(n-butylaminocarbonyloxy)ethyl]hydrazide | 9 | oil | 44.71 | 7.87 | 10.43 | 22.09 | | 44.62 | 7.74 | 10.39 | 21.92 | |
| 103 | 3'-trimethylstannylpropionic acid 2,2-bis[2-(4-chlorophenylaminocarbonyloxy)ethyl]hydrazide | 9 | 178–179 (dec) | 44.61 | 4.99 | 8.67 | | | 44.79 | 5.04 | 8.48 | | |
| 104 | 3'-trimethylstannylpropionic acid 2,2-bis[2-(4-methoxyphenylaminocarbonyloxy)ethyl]hydrazide | 9 | 105–106 (dec) | 49.00 | 6.01 | 8.79 | | | 49.01 | 5.99 | 8.80 | | |
| 105 | 3'-trimethylstannylpropionic acid 2,2-bis[2-methyl-2-(phenylaminocarbonyloxy)ethyl]hydrazide | 9 | 115–125 | 51.59 | 6.33 | 9.25 | 19.60 | | 51.38 | 6.20 | 9.10 | 19.77 | |
| 106 | 3'-trimethylstannylpropionic acid 2,2-bis[2-methyl-2-(cyclohexylaminocarbonyloxy)ethyl]hydrazide | 9 | waxy solid | 50.58 | 8.16 | 9.07 | 19.22 | | 49.79 | 8.13 | 8.61 | 19.60 | |
| 107 | 3'-trimethylstannylpropionic acid 2,2-bis[2-methyl-2-(octadecylaminocarbonyloxy)ethyl]hydrazide | 9 | 55–70 | 62.68 | 10.73 | 5.85 | 12.39 | | 62.56 | 10.56 | 5.92 | 12.85 | |
| 108 | 3'-trimethylstannylpropionic acid 2,2-bis[3-methyl-2-(n-butylaminocarbonyloxy)ethyl]hydrazide | 9 | oil | 46.74 | 8.20 | 9.91 | 21.00 | | 46.69 | 8.38 | 9.65 | 21.55 | |
| 109 | 3'-trimethylstannylpropionic acid 2,2-bis[2-methyl-2-(1-naphthylaminocarbonyloxy)ethyl]hydrazide | 9 | 65–80 | 57.89 | 6.00 | 7.94 | 16.82 | | 58.00 | 6.02 | 7.82 | 16.14 | |
| 110 | 3'-trimethylstannylpropionic acid 2,2-bis[2-methyl-2-(4-methylphenylsulfonyl-aminocarbonyloxy)ethyl]hydrazide | 9 | 78–96 (dec) | 44.16 | 5.56 | 7.36 | 15.58 | 8.42 | 44.07 | 5.56 | 7.09 | 15.07 | 8.41 |
| 111 | 3'-trimethylstannylpropionic acid 2,2-bis[2-methyl-2-(methylaminocarbonyloxy)ethyl]hydrazide | 9 | oil | 39.94 | 7.12 | 11.64 | 24.67 | | 39.37 | 7.14 | 10.97 | 25.24 | |
| 112 | 3'-trimethylstannylpropionic acid 2,2-bis[2-methyl-2-(4-chlorophenylaminocarbonyloxy)ethyl]hydrazide | 9 | 55–70 | 46.32 | 5.38 | 8.31 | | | 46.42 | 5.34 | 8.12 | | |

Table I-continued

| Compound No. | Compound Name | Reaction No. | Melting Point °C. (or Boiling °C.*) | Calculated Value % C | H | N | Sn | S | Found Value % C | H | N | Sn | S |
|---|---|---|---|---|---|---|---|---|---|---|---|---|---|
| 113 | 3'-trimethylstannylpropionic acid 2,2-bis[2-methyl-2-(4-ethoxycarbonylphenylaminocarbonyloxy)ethyl]hydrazide | 9 | 65–75 (dec) | 51.28 | 6.18 | 7.47 | 15.83 | 61.60 | 51.60 | 5.94 | 7.77 | 15.92 | |
| 114 | 3'-trimethylstannylpropionic acid 2,2-bis[2-methyl-2-(3-trifluoromethylphenylaminocarbonyloxy)ethyl]hydrazide | 9 | 50–54 | 45.37 | 4.89 | 7.56 | | | 44.56 | 4.71 | 7.97 | | |
| 115 | 3'-trimethylstannylpropionic acid 2,2-bis[2-methyl-2-(3-chlorophenylaminocarbonyloxy)ethyl]hydrazide | 9 | 46–54 | 46.42 | 5.38 | 8.31 | | | 46.93 | 5.43 | 8.33 | | |
| 116 | 3'-trimethylstannylpropionic acid 2,2-bis[2-methyl-2-(3-methylphenylaminocarbonyloxy)ethyl]hydrazide | 9 | oil | 53.11 | 6.68 | 8.85 | | | 53.02 | 6.88 | 8.52 | | |
| 117 | 3'-trimethylstannylpropionic acid 2,2-bis[2-methyl-2-(4-methoxyphenylaminocarbonyloxy)ethyl]hydrazide | 9 | 51–60 | 50.55 | 6.36 | 8.42 | 17.84 | | 50.61 | 5.95 | 8.10 | 17.50 | |
| 118 | 2'-methyl-3'-trimethylstannylpropionic acid 2,2-bis[2-methyl-2-(phenylaminocarbonyloxy)ethyl]hydrazide | 9 | 46–50 | 52.36 | 6.51 | 9.05 | 19.16 | | 52.26 | 6.68 | 8.63 | 19.83 | |
| 119 | 2'-methyl-3'-trimethylstannylpropionic acid 2,2-bis[2-(tetrahydropyran-2-yloxymethyl)-2-(phenylaminocarbonyloxy)ethyl]hydrazide | 9 | oil | 53.68 | 6.76 | 6.96 | 14.73 | | 53.08 | 6.89 | 6.45 | 14.91 | |
| 120 | 3'-trimethylstannylpropionic acid 2,2-bis[2-n-decyl-2-(phenylaminocarbonyloxy)ethyl]hydrazide | 9 | 40–70 | 61.61 | 8.70 | 6.53 | 13.84 | | 61.90 | 8.63 | 6.29 | 13.73 | |
| 121 | 3'-trimethylstannylpropionic acid 2,2-bis[2-n-hexyl-2-(phenylaminocarbonyloxy)ethyl]hydrazide | 9 | 40–80 | 58.00 | 7.84 | 7.51 | 15.92 | | 57.98 | 7.85 | 7.36 | 15.85 | |
| 122 | 3'-trimethylstannylpropionic acid 2,2-bis[2-methoxymethyl-2-(phenyl)aminocarbonyloxy)ethyl]hydrazide | 9 | oil | 50.55 | 6.36 | 8.42 | 17.84 | | 51.07 | 6.55 | 8.10 | 17.62 | |
| 123 | 3'-trimethylstannylpropionic acid 2,2-bis[2-ethyl-2-(phenylaminocarbonyloxy)ethyl]hydrazide | 9 | 30–60 | 53.10 | 6.68 | 8.84 | 18.74 | | 52.98 | 6.76 | 8.65 | 18.85 | |
| 124 | 3'-trimethylstannylpropionic acid 2,2-bis[2-phenyl-2-(phenylaminocarbonyloxy)ethyl]hydrazide | 9 | 45–75 | 59.27 | 5.80 | 7.68 | 16.27 | | 57.94 | 6.04 | 7.68 | 16.46 | |
| 125 | 3'-trimethylstannylpropionic acid 2,2-bis[2-(4-methoxyphenoxymethyl)-2-(phenylaminocarbonyloxy)ethyl]hydrazide | 9 | 35–47 | 56.55 | 5.93 | 6.59 | 13.97 | | 56.55 | 5.99 | 6.53 | 15.15 | |
| 126 | 3'-trimethylstannylpropionic acid 2,2-bis[2-phenylaminocarbonyloxy)cyclohexyl]hydrazide | 9 | 55–82 | 56.07 | 6.76 | 8.17 | | | 51.95 | 6.88 | 9.53 | | |
| 127 | 3'-tri-n-butylstannylpropionic acid 2-[(phenylamino)carbonyl]hydrazide | 2 | 96–98 | 53.24 | 7.92 | 8.47 | 23.92 | | 53.22 | 7.84 | 8.46 | 23.72 | |
| 128 | 3'-tri-n-butylstannylpropionic acid 4-methylphenylmethylenehydrazide | 1a | 35–37 | 57.63 | 8.41 | 5.84 | 24.76 | | 57.76 | 8.51 | 5.84 | 24.77 | |
| 129 | 3'-tri-n-butylstannylpropionic acid 4-methoxyphenylmethylenehydrazide | 1a | oil | 56.59 | 8.31 | 5.50 | 23.30 | | 56.78 | 8.21 | 5.50 | 23.34 | |
| 130 | 3'-tri-n-butylstannylpropionic acid 2-[(phenylamino)thioxomethyl]hydrazide | 2 | 55–65 | 51.58 | 7.67 | 8.20 | 23.17 | 6.26 | 51.44 | 7.55 | 8.03 | 23.11 | 6.17 |
| 131 | 3'-tri-n-butylstannylpropionic acid 2-benzoylhydrazide | 3 | 84–86 | 54.91 | 7.96 | 5.82 | 24.66 | | 54.95 | 7.97 | 5.69 | 24.17 | |
| 132 | 3'-tri-n-butylstannylpropionic acid 2,2-bis[2-methyl-2-(phenylaminocarbonyloxy)ethyl]hydrazide | 9 | 50–80 | 57.46 | 7.71 | 7.66 | 16.22 | | 57.40 | 7.43 | 8.12 | 16.44 | |
| 133 | 3'-trimethylstannylpropionic acid 2,2-bis(2-hydroxyethyl)hydrazide | 7 | oil | 35.43 | 7.14 | 8.26 | 35.01 | | 35.02 | 7.07 | 7.89 | 34.94 | |
| 134 | 3'-trimethylstannylpropionic acid 2,2-bis(2-hydroxy-3-methoxypropyl)hydrazide | 7 | oil | 39.37 | 7.55 | 6.56 | 27.79 | | 39.04 | 7.59 | 6.17 | 27.40 | |
| 135 | 3'-trimethylstannylpropionic acid 2,2-bis[2-hydroxy-3-(tetrahydropyran-2-yloxy)propyl]hydrazide | 7 | oil | 46.58 | 7.82 | 4.94 | 20.92 | | 46.60 | 7.99 | 4.92 | 20.38 | |
| 136 | 3'-trimethylstannylpropionic acid 2,2-bis(2-hydroxybutyl)hydrazide | 7 | oil | 42.56 | 8.16 | 7.09 | 30.04 | | 42.08 | 8.00 | 7.27 | 29.44 | |
| 137 | 3'-trimethylstannylpropionic acid 2,2-bis(2-hydroxyoctyl)hydrazide | 7 | 30–45 | 52.08 | 9.54 | 5.52 | 23.39 | | 52.28 | 9.64 | 5.35 | 22.60 | |
| 138 | 3'-trimethylstannylpropionic acid 2,2-bis(2-hydroxydodecyl)hydrazide | 7 | 35–50 | 58.16 | 10.41 | 4.52 | 19.15 | | 57.98 | 10.11 | 4.30 | 19.21 | |
| 139 | 3'-tri-n-butylstannylpropionic acid | | | | | | | | | | | | |

Table I-continued

| Compound No. | Compound Name | Reaction No. | Melting Point °C. (or Boiling °C.*) | Calculated Value % C | H | N | Sn | S | Found Value % C | H | N | Sn | S |
|---|---|---|---|---|---|---|---|---|---|---|---|---|---|
| | 2,2-bis(2-hydroxypropyl)hydrazide | 7 | oil | 51.13 | 9.40 | 5.68 | 24.06 | | 50.61 | 9.49 | 5.57 | 24.51 | |
| 140 | 3'-trimethylstannylpropionic acid 2,2-bis(2-hydroxypropyl)hydrazide | 7 | oil | 39.26 | 7.69 | 7.63 | 32.33 | | 39.26 | 7.74 | 7.44 | 32.36 | |
| 141 | 2'-methyl-3'-trimethylstannylpropionic acid 2,2-bis(2-hydroxypropyl)hydrazide | 7 | oil | 40.97 | 7.93 | 7.35 | 31.14 | | 40.85 | 7.99 | 7.30 | 31.13 | |
| 142 | 3'-trimethylstannylpropionic acid 2,2-bis(2-hydroxycyclohexyl)hydrazide | 7 | oil | 48.34 | 8.11 | 6.26 | 26.54 | | 45.22 | 7.94 | 6.56 | 23.69 | |
| 143 | 3'-trimethylstannylpropionic acid 3,3-bis(2-hydroxy-2-phenylethyl)hydrazide | 7 | oil | 53.79 | 6.57 | 5.70 | 24.16 | | 53.37 | 6.72 | 6.12 | 24.66 | |
| 144 | 3'-trimethylstannylpropionic acid 2,2-bis[2-hydroxy-3-(4-methoxyphenoxy)propyl]hydrazide | 7 | 97–100.5 | 51.08 | 6.59 | 4.58 | 19.41 | | 51.54 | 6.55 | 4.57 | 19.33 | |
| 145 | 2,6-dimethyl-4-(2'-trimethylstannylethylcarbonylamino)morpholine | 10 | (118–120 @ 27 Pa) | 41.29 | 7.51 | 8.03 | 34.00 | | 40.69 | 7.40 | 7.85 | 33.67 | |
| 146 | 3-tri-n-butylstannylpropionic acid hydrazide | | oil | 47.77 | 9.09 | 7.43 | 31.47 | | 47.78 | 9.10 | 7.14 | 31.67 | |
| 147 | 2-methyl-3-trimethylstannylpropionic acid hydrazide | | (107 @ 27 Pa) | 31.74 | 6.85 | 10.57 | 44.80 | | 31.30 | 6.95 | 10.16 | 44.48 | |
| 148 | 3-trimethylstannylpropionic acid hydrazide | | 92–98 @ 8–11 Pa) | | | | | | | | | | |
| 149 | 3'-trimethylstannylpropionic acid 2-[2-(4-t-butylphenylsulfonyl)ethyl]hydrazide (A) + 3'-trimethylstannylpropionic acid 1-[1-(4-t-butylphenylsulfonyl)ethyl]hydrazide (B) | 11 | oil | 45.49 | 6.79 | 5.89 | 24.97 | 6.75 | 45.48 | 6.70 | 5.71 | 24.78 | 6.67 |
| 150 | Hexahydro-1,3,5-tris(2-trimethylstannylethylcarbonylamino)-1,3,5-triazene | 1a | (120–126 @ 13.3 Pa) | 31.98 | 6.13 | 10.65 | 45.14 | | 31.21 | 6.18 | 10.36 | 44.96 | |

*(dec) indicates compound decomposes at that temperature

Other compounds of the present invention that may be prepared according to the methods described herein include the following:

6'-trimethylstannylhexanoic acid 1-methyl-2,2-bis[2-methyl-2-phenylaminocarbonyloxy)ethyl]hydrazide;
6'-trimethylstannylhexanoic acid 1-n-butyl-2-(bicyclo[2.2.1]hept-2-ylcarbonyl)-2-(2-cyanoethyl)hydrazide;
3'-trimethylstannylpropionic acid 1-n-octyl-2-(2-ethoxycarbonylethyl)-2-(1-naphthoyl)hydrazide;
3'-trimethylstannylpropionic acid 1-(2-hydroxyethyl)-2-(3-phenyl-2-pentenoyl)-2-(3-n-octyloxycarbonylpropyl)hydrazide;
3'-trimethylstannylpropionic acid 1-(2-hydroxyoctyl)-2-(4-bromobenzoyl)-2-(n-butanoyl)hydrazide;
3'-trimethylstannylpropionic acid 1-(2-cyanoethyl)-2-n-nonanoyl-2-(2-methyl-2-phenylpropanoyl)hydrazide;
3'-trimethylstannylpropionic acid 1-(2-ethoxycarbonylethyl)-2-benzoyl-2-(4-octylbenzoyl)hydrazide;
trimethylstannylacetic acid 1-(2-n-butoxycarbonylethyl)-2-(2-naphthoyl)-2-(4-n-octyloxybenzoyl)hydrazide;
trimethylstannylacetic acid 1-(n-butanoyl)-2-methyl-2-(phenoxycarbonyl)hydrazide;
trimethylstannylacetic acid 1-(n-nonanoyl)-2-n-pentyl-2-(4-hydroxybenzoyl)hydrazide;
6'-trimethylstannylhexanoic acid 1-benzoyl-2-n-octyl-2-(4-cyanobenzoyl)hydrazide;
6'-trimethylstannylhexanoic acid 1-naphthoyl-2-(2-hydroxyoctyl)2-(N,N-di-n-octylaminocarbonyl)hydrazide;
trimethylstannylacetic acid 1-methyl-2-benzoyl-2-[N-(2,3-dimethyl-2-butenyl)-n-octylaminocarbonyl]hydrazide;
trimethylstannylacetic acid 1-n-octyl-2-(1-naphthoyl)-2-[N-cyclopropyl(2-hydroxyethyl)aminocarbonyl]hydrazide;
trimethylstannylacetic acid 1-(2-hydroxypropyl)-2-methyl-2-[N-benzoylbicyclo[2.2.1]hept-2-ylaminocarbonyl]hydrazide;
3'-trimethylstannylpropionic acid 1-(2-ethoxycarbonylethyl)-2-n-octyl-2-[N-(2-ethoxycarbonylethyl)(2-n-hexyloxycarbonylethyl)aminocarbonyl]hydrazide;
3'-trimethylstannylpropionic acid 1-(4-ethoxycarbonylbutyl)-2-(3-propoxycarbonylpropyl)-2-[(N-4-dodecylphenyl-2-hydroxycyclohexylamino)carbonyl]hydrazide;
3'-trimethylstannylpropionic acid 1-n-butanoyl-2-n-pentanoyl-2-[(N-3-t-butoxyphenyl-n-octanoylamino)thioxomethyl]hydrazide;
6'-trimethylstannylhexanoic acid 1-n-octanoyl-2-(2-hydroxyoctyl)2-[(N-4-bromophenyl-1-naphthoylamino)thioxomethyl]hydrazide;
6'-trimethylstannylhexanoic acid 1-benzoyl-2-(2-hydroxyethyl)-2-[N-4-cyanophenylmethylamino)thioxomethyl]hydrazide;
6'-trimethylstannylhexanoic acid 1-napthoyl-2-ethyl-2-[(N-cyclopentyl-n-pentylamino)thioxomethyl]hydrazide;
trimethylstannylacetic acid 1-methyl-2,2-(1,4-tetramethylene)hydrazide;
3'-trimethylstannylpropionic acid 1-n-octyl-2,2-diheptadecylhydrazide;

3'-trimethylstannylpropionic acid 1-methyl-2-methyl-2-(2-n-butoxyethyl)hydrazide;

3'-trimethylstannylpropionic acid 1-methyl-2-methyl-2-(4-n-pentyloxybenzyl)hydrazide;

3'-trimethylstannylpropionic acid 1-ethyl-2-[2-(4-bromophenylsulfonyl)ethyl]-2-methylhydrazide;

3'-trimethylstannylpropionic acid 1-n-butyl-2-[2-(4-ethylphenylsulfonyl)ethyl]-2-methylhydrazide;

3'-trimethylstannylpropionic acid 1-(2-hydroxyethyl)-2-methyl-2-[2-(4-octadecylphenylsulfonyl)ethyl]hydrazide;

3'-trimethylstannylpropionic acid 1-n-octyl-2-[(4-biphenylylsulfonyl)ethyl]-2-methylhydrazide;

6'-trimethylstannylhexanoic acid 1-benzoyl-2-methyl-2-[2-(4-naphthylphenylsulfonyl)ethyl]hydrazide;

6'-trimethylstannylhexanoic acid 1-nonanoyl-2-methyl-2-[2-(4-i-propoxyphenylsulfonyl)ethyl]hydrazide;

6'-trimethylstannylhexanoic acid 1-methyl-2-methyl-2-[2-(4-phenoxyphenylsulfonyl)ethyl]hydrazide;

trimethylstannylacetic acid 1-n octyl-2,2-bis[2-(1-naphthyl)-2-(cyclopropylaminocarbonyloxy)ethyl]hydrazide;

trimethylstannylacetic acid 1-methyl-2,2-bis[2-butoxy-2-(N-bicylo[2.2.1]hept-2-yl-N-methylaminocarbonyloxy)ethyl]hydrazide;

trimethylstannylacetic acid 1-(8-hydroxyoctyl)-2,2-bis[2-(4-n-propoxyphenyl-2-(N-n-butyl-N-4-fluorophenylaminocarbonyloxy)ethyl]hydrazide;

6'-trimethylstannylhexanoic acid 1-(4-hydroxybutyl)-2,2-bis-[2-(N-octadecyl-4-hexylphenylaminocarbonyloxy)cyclopropylene]hydrazide;

6'-trimethylstannylhexanoic acid 1-methyl-2,2-bis[2-n-decyl-2-(4-n-butoxyphenylaminocarbonyloxy)ethyl]-hydrazide;

6'-trimethylstannylhexanoic acid 2,2-bis[2-(N-methyl-4-n-pentyloxy carbonylphenylaminocarbonyloxy)ethyl]hydrazide;

6'-trimethylstannylhexanoic acid 2,2-bis[2-(N-methyl-4-ethylsulfonylphenylaminocarbonyloxy)ethyl]hydrazide;

6'-trimethylstannylhexanoic acid 1-methyl-2,2-bis[2-(N-methyl-4-n-butylsulfonylphenylaminocarbonyloxy)ethyl]hydrazide;

trimethylstannylacetic acid 1-methyl-2-(1-cyclopropyl-)ethylidenehydrazide;

trimethylstannylacetic acid 1-n-propyl-2-[1-(1-methyl-1-phenyl-ethyl)propylidene]hydrazide;

trimethylstannylacetic acid 1-n-octyl-2-(2-ethyl-1-n-octyl-3-phenyl-2-propenylidene)hydrazide;

trimethylstannylacetic acid (4-n-octyloxyphenylmethylene)hydrazide;

3'-trimethylstannylpropionic acid 2-(1-naphthoxy)ethylidenehydrazide;

3'-trimethylstannylpropionic acid 1-methyl-2-[(2-benzyloxyethylidene]hydrazide;

3'-trimethylstannylpropionic acid 1-methyl2-(4-N,N-di-n-butylaminophenylmethylene)hydrazide;

3'-trimethylstannylpropionic acid 1-methyl-2-[2-(n-heptylcarbonylamino)ethylidene]hydrazide;

3'-trimethylstannylpropionic acid 1-methyl-2-[2-(1-naphthylcarbonylamino)ethylidene]hydrazide; and 3'-trimethylstannylpropionic acid 1-methyl-2-(cyclopropylidene)hydrazide.

The fifty compounds listed in the preceding paragraph are all analogs of the compounds listed in Table I and can be made using the latter compounds as starting materials and reacting them with appropriate reactants to replace one or more of the remaining reactive hydrogen atoms that are attached to the neighboring two nitrogen atoms or are on the moieties that are attached to said nitrogen atoms. Non-limiting examples of appropriate reactants are alpha, beta- unsaturated carbonyl compounds, for example, acrylic acid and alkyl acrylates, or acrylonitrile, vinyl sulfones, alkyl halides, acyl halides, aroyl halides, oxiranes, acrolein, or alkyl- or aryl- type vinyl sulfones. Further examples include ethyl acrylate, butyl acrylate, benzenesulfonyl ethylene, methyl vinyl ketone, octyl vinyl ketone, phenyl vinyl ketone, methyl iodide, octyl bromide, octadecyl bromide, 8-bromooctanol, acetyl chloride, nonanoyl chloride, benzoyl chloride, ethylene oxide, 1,2-epoxyoctane, and cyclohexene oxide.

The compounds of the present invention are particularly useful for the control of those larvae of Lepidoptera and larvae and adults of Coleoptera that feed on plant foliage. The compounds are best applied as sprays directly to the infested foliage of the plants being attacked. The observed effect is a cessation of feeding shortly after application followed by death of the insect.

The rates used to protect plants must be kept below that level which will cause injury to the plant but must be effective in control of the pests. Under field conditions, rates between 1 oz. and 8 oz. of active ingredient per acre (70 to 560 gms/hectare) applied in sufficient water to provide coverage of the foliage have been successfully used.

The compounds have a moderate residual life on foliage. Where infestation from the particular pest continues, repeated applications to the foliage at suitable intervals may be necessary to protect the crop.

It is well known that in areas where insecticides have been repeatedly applied for a number of years, certain strains of insects have been increasingly difficult to control. It has been found, however, that these same insect strains succumb readily to the compounds of the present invention when applied to the foliage of the host plant.

Application of the compounds of the present invention as insecticides can be carried out in a number of ways. For practical applications, the compounds of the invention can be used alone, or dissolved or suspended in suitable carriers such as water, alcohols, ketones, phenols, toluene, or xylenes. Optionally, one or more surface active agents and/or inert diluents can be added to the formulations to facilitate handling. The formulations can take the form of dusts, granules, wettable powders, pastes, emulsifiable concentrates, aerosols, water solution concentrates, or water soluble solids. For example, the compounds of the invention can be applied as dusts when admixed with or absorbed on powdered solid carriers, such as the various mineral silicates, e.g., mica, talc, pyrophillite, and clays, or as liquids or sprays when in a liquid carrier, as in solution in a suitable solvent such as acetone, benzene, or kerosene, or dispersed in a suitable non-solvent medium, for example, water. The compounds of the present invention may be mixed with surface-active dispersing agents (see, e.g., U.S. Pat. No. 2,547,724, columns 3 and 4), with or without an organic solvent, as concentrates for subsequent addition of water to make aqueous suspensions of the chemicals of the desired concentration. The compounds of the present invention may be admixed with powdered solid carriers, such as mineral silicates together with a surface-active dispersing agent so that a wettable powder is obtained, or may be shaken with water to form a suspension of a compound of the present invention and the powdered solid carrier in water for application in that form. The compounds of the present invention may also be applied by the aerosol method. Solutions for aerosol treatment may be prepared by dissolving the chemical directly in the aerosol carrier which is liquid under pressure but which is a gas at ambient temperature (e.g., 20° C.) and atmospheric pressure, or the aerosol solution may be prepared by first dissolving the chemical in a less volatile solvent and then admixing such solution with the highly volatile liquid aerosol carrier. The compounds of the present invention may also be used admixed with carriers that are active themselves, for example, other insecticides or acaricides.

Formulations of compounds of the present invention should contain amounts of the compound that will be effective for the particular method of insect control to be used. Their amounts can vary widely; typically the range is from 0.1 to 95% active ingredient when it is prepared in concentrate form. Subsequent dilutions to a spray dilution can contain a few parts per million (in certain cases, for very active compounds, one part per million) when used as a dilute spray to full strength concentrates when applied by ultra low volume techniques.

The following examples will serve to illustrate the preparation and properties of the compounds of the present invention.

EXAMPLE 1

3-trimethylstannylpropionic acid hydrazide 3-trimethylstannylpropionic acid hydrazide, one of the starting compounds employed for the preparation of the N-substituted triorganostannylhydrocarbyl carboxylic acid hydrazides of the present invention was prepared using the following procedure:

A mixture of 8.0 g (0.030) mole of 2-(ethyoxycarbonyl) ethyltrimethylstannane and 5 ml of 95% hydrazine (0.15 mole) in 10 ml of ethanol was refluxed for 2 hours. The volatiles were removed at reduced pressure. Distillation of the crude product afforded 5.26 g of 3-trimethylstannylpropionic acid hyrazide, Compound 148 of Table I (wherein melting points and boiling points of various compounds that were prepared are listed). The infrared spectrum (neat) of the distillate showed the following characteristic absorptions: 3300 cm$^{-1}$ (N—H), 1660 cm$^{-1}$ and

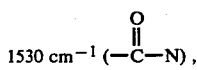

1530 cm$^{-1}$ (—C—N), and 760 cm$^{-1}$ (—Sn(CH$_3$)$_3$). A gas chromatogram of the sample showed a single peak on a 189 mm × 3.2 mm commercially obtained column packed with 10% of silicone gum rubber on silanized diatomaceous earth. The NMR spectrum (CDCl$_3$) exhibited the following proton absorptions: a broad singlet at 7.52 delta (1H, N—H); a singlet at 3.88 delta (2H, NH$_2$); a triplet centered at 2.35 delta (2H, —COCH$_2$); a triplet centered at 0.98 delta (2H, CH$_2$—Sn); and a singlet at 0.06 delta (9H, Sn(CH$_3$)$_3$) flanked by the J($^{117/119}$Sn—CH$_3$) doublets.

Using the procedure described in the preceding paragraph, two additional analogs of the compound of Example 1 were prepared; these compounds are listed in Table I as Compounds 146 and 147.

EXAMPLE 2

3'-trimethylstannylpropionic acid 1-methylethylidenehydrazide 4.0 g (0.016 mole) of 3-trimethylstannylpropionic acid hydrazide of Example 1 and 5.0 ml (0.068 mole) of reagent grade acetone were placed in a 50 ml single-neck flask equipped with a stirrer. The flask was stoppered and the solution was then stirred for about fifteen minutes, at which time the reaction mixture turned solid. Recrystallization of the air-dried solid from acetone-water mixture containing 50% by weight of acetone gave 3.8 g of 3-trimethylstannylpropionic acid 1-methylethylidenehydrazide, Compound 1 of Table I. The infrared spectrum (KBr disc) showed the characteristic bands at 3200 and 3050 cm$^{-1}$ for N—H and at 1655 and 1550 cm$^{-1}$ for carbonyl absorption of

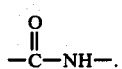

—C—NH—.

The carbon-tin bond was characterized by infrared absorption bands at 760, 522, 515 and 503 cm$^{-1}$. Nuclear magnetic resonance spectroscopy suggested that the compound exists as a tautomeric mixture in CDCl$_3$ solution with one form predominating over the other. The NMR spectra of the dominant isomer showed the following: a broad singlet at 8.38 delta (1H, N—H); a triplet centered at 2.82 delta (2H, —CH$_2$CO); two 3-proton signlets at 1.82 delta and 1.92 delta (—N=C(CH$_3$)$_2$); a triplet centered at 1.02 delta (2H, —CH$_2$Sn); a singlet at 0.06 delta (9H, Sn(CH$_3$)$_3$) flanked by the J($^{117/119}$Sn—CH$_3$) doublets.

Using the procedure and apparatus described in the preceding paragraph, additional acid hydrazides were prepared using cyclohexanone, acetophenone and 1,3-diphenyl-2-propanone, respectively, as the starting ketone to form 3-trimethylstannylpropionic acid cyclohexylidenehydrazide, Compound 2 of Table I, 3'-trimethylstannylpropionic acid (1-phenylethylidene)hydrazide, Compound 14 of Table I; and 3'-trimethylstannylpropionic acid (1,3-diphenyl-2-propylidene)hydrazide, Compound 23 of Table I.

EXAMPLE 3

3-trimethylstannylpropionic acid phenylmethylenehydrazide

In the manner described in Example 2, 3.0 g (0.012 mole) of 3-trimethylstannylpropionic acid hydrazide was reacted with 1.5 ml (0.015 mole) of benzaldehyde in 2.0 ml of ethanol. Recrystallization of the solid product from 95% ethanol gave 3.6 g of 3-trimethylstannylpropionic acid phenylmethylenehydrazide, Compound 3 of Table I. The infrared spectrum (KBr disc) showed N—H absorptions at 3100 cm$^{-1}$ and a carbonyl band at 1670 cm$^{-1}$. The carbon-tin bond gave characteristic absorptions at 770, 540, 520 and 505 cm$^{-1}$. NMR spectroscopy (CDCl$_3$) showed the following: the singlet at 10.43 delta (1H, N—H); a broadened singlet at 7.87 delta (1H, —N=CHPh); the aromatic protons formed two complex bands, 2H ortho centered at 7.64 delta and 3H meta and para centered at 7.38 delta; a triplet centered at 2.99 delta (2H, COCH$_2$); a triplet centered at 1.11 delta (2H, SnCH$_2$); and a singlet at the 0.14 delta (9H, Sn(CH$_3$)$_3$) flanked by the J($^{117/119}$Sn—CH$_3$) doublets.

Using the procedure described in the preceding paragraph, Compounds 4–13, 15–22, 24–39, 128 and 129 of Table I were prepared by reacting a trialkylstannylpropionic acid hydrazide with the appropriate aldehyde.

EXAMPLE 4

3'-trimethylstannylpropionic acid 2-[(phenylamino)carbonyl]hydrazide

A solution containing 2.51 g (0.01 mole of 3-trimethylstannylpropionic acid hydrazide in 30 ml of anhydrous tetrahydrofuran (THF) was placed in a three-neck glass flask equipped with a condenser, a stirrer and a dropping funnel. 1.2 g (0.01 mole) of phenylisocyanate was added, very slowly, to the solution at room temperature under a blanket of nitrogen. The reaction mixture was stirred for 20 minutes and then heated at reflux for two hours, after which the solvent, THF, was stripped off under reduced pressure. The resultant crystalline solid was crystallized from an equeous ethanol solution containing 50% by volume of ethanol yielding 3.55 g (96% yield) of 3'-trimethylstannylpropionic acid 2-[(phenylamino)carbonyl]hydrazide, Compound 41 of Table I. The infrared spectrum (Nujol, trademark of Schering Plough Corporation for a mixture of liquid hydrocarbons from petroleum) showed the following characteristic absorptions: 3280 and 3200 cm$^{-1}$ (N—H), 1695 and 1650 cm$^{-1}$ (carbonyl), and 750 and 690 cm$^{-1}$ (aromatic). The NMR spectrum (CDCl$_3$) exhibited the following absorptions: multiplets centered at 9.36 delta and 8.25 delta (N—H); multiplets centered at 7.50 delta and 7.25 delta (5H, aromatic protons); a triplet centered at 2.42 delta (2H, —CH$_2$CO); a triplet centered at 0.90 delta (2H, CH$_2$Sn); and a singlet at 0.01 delta (9H, Sn(CH$_3$)$_3$) flanked by the J($^{117/119}$Sn—CH$_3$) doublets. Subsequent exchange with D$_2$O revealed that one N—H absorption was hidden under the phenyl bands.

Using the procedure described in the preceding paragraph, additional compounds which are analogs of Compound 41 were prepared employing the appropriate reagents. These compounds are listed in Table I as Compounds 40, 42–58, 93 and 127.

EXAMPLE 5

3'-trimethylstannylpropionic acid 2[(phenylamino)thioxomethyl]hydrazide

A solution of 2.51 g (0.01 mole) of 3-trimethylstannylpropionic acid hydrazide in 40 ml of 95% ethanol was placed in a three-neck flask equipped with a condenser, a stirrer and a dropping funnel. 1.36 g (0.01 mole) of phenylisothiocyanate was added, very slowly, at room temperature. The reaction mixture was stirred for 20 minutes and during the next two hours was gradually heated and then refluxed. The ethanol was distilled off and the resultant product was recrystallized from an aqueous ethanol solution containing 50% by volume of ethanol to give 3.65 g (94% yield) of 3'-trimethylstannylpropionic acid 2[(phenylamino)thioxomethyl]hydrazide, Compound 59 of Table I. The infrared spectrum Nujol) showed the following characteristic absorptions: 3150 and 3050 cm$^{-1}$ (N—H); 1675 and 1670 cm$^{-1}$ (C=O); and 740 and 690 cm$^{-1}$ (aromatic). The NMR spectrum (CD$_3$COCD$_3$) exhibited the following absorptions: a singlet at 9.17 delta (N—H); a multiplet centered at 7.35 delta (5H, aromatic protons); a triplet centered at 2.58 delta (—CH$_2$CO); a triplet centered at 0.94 delta (CH$_2$—Sn); and a singlet at 0.08 delta (9H, Sn(CH$_3$)$_3$) flanked by the J($^{117/119}$Sn—CH$_3$) doublets.

Using the procedure described in the preceding paragraph, additional analog compounds of Compound 59 were prepared employing appropriate reagents. These compounds are listed in Table I as Compounds 60–68 and 130.

EXAMPLE 6

3'-trimethylstannylpropionic acid 2-(benzoyl) hydrazide

A solution of 2.51 g (0.01 mole) of 3-trimethylstannylpropionic acid hydrazide in 40 ml of anhydrous tetrahydrofuran (THF) and 10 ml of triethylamine was placed in a three-neck flask equipped with a condenser, a stirrer and a dropping funnel. 1.41 g (0.01 mole) of benzoyl chloride dissolved in 10 ml of anhydrous THF was added slowly to the solution under a nitrogen blanket. The resultant cloudy mixture was stirred at room temperature for thirty minutes and then warmed slowly up to 40° C. After 30 minutes, the reaction mixture was cooled and the solid removed by filtration. The filtrate was evaporated under reduced pressure to yield a crude solid product which was recrystallized from an aqueous ethanol solution containing 50% by volume of ethanol to give 3.3 g (93% yield) of white needles of 3'-trimethylstannylpropionic acid 2-benzoylhydrazide, Compound 89 of Table I. The infrared spectrum (Nujol (Trademark)) showed the following characteristic absorptions: 3150 and 3100 cm$^{-1}$ (N—H); 1680 and 1640 cm$^{-1}$ (C=O); and 760 and 705 cm$^{-1}$ (aromatic). The NMR spectrum (CDCl$_3$) exhibited the following absorptions: doublets centered at 10.03 delta and 9.50 delta (2H, N—H); multiplets centered at 7.83 delta and 7.38 delta (5H, aromatic protons); a triplet centered at 2.50 delta (—CH$_2$CO); a triplet centered at 0.98 delta (—CH$_2$Sn); and a singlet at 0.04 delta (9H, Sn(CH$_3$)$_3$) flanked by the J($^{117/119}$Sn—CH$_3$) doublets.

Using the procedure detailed in the preceding paragraph, additional analog compounds of Compound 89 were prepared employing appropriate reagents. These compounds are listed in Table I as Compounds 69–88, 92, 94 and 131.

EXAMPLE 7

3'-trimethylstannylpropionic acid 2-(2-carboxybenxoyl)hydrazide

A solution of 3.55 g (0.024 mole) of phthalic anhydride in 25 ml of tetrahydrofuran was added dropwise over a period of twenty-five minutes to a solution of 6.0 g (0.024 mole) of 3-trimethylstannylpropionic acid hydrazide and 10 ml of dry tetrahydrofuran in a 100 ml single-neck flask fitted with a magnetic stir bar. After removal of solvent by means of a rotary evaporator, there remained 9.4 g of a solid 3'-trimethylstannylpropionic acid 2-(2-carboxybenzoyl)hydrazide, Compound 95 of Table I. The infrared spectrum (KBr disc) showed the characteristic broad absorptions for carboxyl OH from 3500 cm$^{-1}$ to 2500 cm$^{-1}$. The broadened carbonyl bands were found at 1710 cm$^{-1}$ (carboxylic acid) and at 1660 and 1610 cm$^{-1}$ (hydrazide). The carbon-tin bond gave characteristic absorptions at 760, 520 and 505 cm$^{-1}$. The NMR spectrum (DMSOd$_6$) showed the following: a very broad peak at 12.90 delta (1H, COOH); two singlets at 10.08 delta and 9.91 delta (2H, N—H); two complex multiplets centered at 7.80 delta and 7.60 delta (4H, aromatic); a triplet centered at 2.42 delta (2H, —CH$_2$CO); a triplet centered at 0.94 delta (2H, —CH$_2$Sn); and a singlet at 0.09 delta (9H, Sn(CH$_3$)$_3$) flanked by the J($^{117/119}$Sn—CH$_3$) doublets.

EXAMPLE 8

3'-trimethylstannylpropionic acid 2-(2-carboxybenzoylhydrazide, sodium salt

The compound of Example 7 was converted to its sodium salt by stirring an aqueous slurry of 4.6 g (0.012 mole) of Compound 95 with an equimolar amount of sodium bicarbonate. The reaction mixture was stirred at room temperature for one-half hour and at 50° C. for one hour. The reaction mixture was filtered at reduced pressure. The residue consisted of 2.7 g of a white solid, the sodium salt of 3'-trimethylstannylpropionic acid 2-(2-carboxybexzoyl)hydrazide, Compound 96 of Table I. The infrared spectrum (KBr disc) showed the carboxylate (—COO$\theta$) function as a strong band at 1400 cm$^{-1}$. The NMR spectrum (DMSOd$_6$) consisted of the following: two complex multiplets centered at 7.61 delta and 7.36 delta (4H, aromatic); a triplet centered at 2.41 delta (2H,—CH$_2$C=O); a triplet centered at 0.94 delta (2H,—CH$_2$Sn); and a singlet at 0.08 delta (9H, Sn(CH$_3$)$_3$) flanked by the J($^{117/119}$Sn—CH$_3$) doublets.

EXAMPLE 9

3'-trimethylstannylpropionic acid 2,2-bis(2-hydroxypropyl)hydrazide

A solution containing 125 g (0.50 mole) of 3-trimethylstannylpropionic acid hydrazide in 300 ml of aqueous ethanol solution containing 50% by volume of ethanol was placed in a three-neck flask equipped with a condenser, a stirrer and a dropping funnel. 90 ml (1.3 mole) of propylene oxide was added slowly at room temperature, and the reaction mixture was stirred for eight hours followed by heating to 40° C. for eight hours. Solvent was then stripped off under reduced pressure at 80° C. The viscous liquid product was dried under a vacuum (13.3 Pa) at 60°–80° C. for two hours to remove the final traces of ethanol and water to yield 181 g (98.5% yield) of a viscous liquid, 3'-trimethylstannylpropionic acid 2,2-bis(2-hydroxypropyl)hydrazide, Compound 140 of Table I. The infrared spectrum (neat) showed the following absorptions: 3350 cm$^{-1}$ (OH); 3200 cm$^{-1}$ (N—H) and 1650 cm$^{-1}$ (C=O).

Using the procedure detailed in the preceding paragraph, additional analog compounds of Compound 140 were prepared employing appropriate reagents. These compounds are listed in Table I as Compounds 133–139 and 141–144.

EXAMPLE 10

3'-trimethylstannylpropionic acid 2,2-bis[2-methyl-2-(phenylaminocarbonyloxy)ethyl]hydrazide A solution containing 147 g (0.40 mole) of 3'-trimethylstannylpropionic acid 2,2-bis(2-hydroxypropyl)hydrazide (Compound 140 of Example 9) in 350 ml of dry tetrahydrofuran was placed in a three-neck flask equipped with a condenser, a stirrer and a dropping funnel. 9.6 g (0.80 mole) of phenylisocyanate in 100 ml of dry tetrahydrofuran was added slowly at room temperature under a blanket of nitrogen. The reaction mixture was stirred for thirty minutes followed by heating at reflux (70° C.) for four hours. The solvent was then removed under reduced pressure yielding 240 g (99% yield) of a thick viscous liquid which formed a glassy solid at room temperature, 3'-trimethylstannylpropionic acid 2,2-bis[2-methyl-2-(phenylaminocarbonyloxy)ethyl]hydrazide, Compound 105 of Table I. The infrared spectrum (Nujol) showed the following absorptions: 3250 and 3190 cm$^{-1}$ (N—H); 1700 and 1650 cm$^{-1}$ (C=O); 760 and 695 cm$^{-1}$ (aromatic). The NMR spectrum (CDCl$_3$) showed the following: a broad singlet at 7.52 delta (N—H); a multiplet centered at 4.96 delta (CHOCO); a multiplet centered at 3.24 delta (C-CH$_2$—N); a triplet centered at 2.27 delta (—CH$_2$CO—); a multiplet centered at 0.98 delta (—CH$_2$—Sn); and a singlet at 0.10 delta (9H, Sn(CH$_3$)$_3$) flanked by the J($^{117/119}$Sn—CH$_3$) doublets.

Using the procedure described in the preceding paragraph and the appropriate intermediate hydrazide alcohols made following the procedure of Example 9, additional analogs were prepared. These analogs are listed in Table I as Compounds 100–104, 106–126 and 132.

EXAMPLE 11

3'-trimethylstannylpropionic acid 2-(2-hydroxycyclohexyl)hydrazide 10 g (0.040 mole) of 3-trimethylstannylpropionic acid hydrazide, 4.1 g (0.042 mole) of cyclohexene oxide and 50 ml of aqueous ethanol containing 80% by volume of ethanol was placed in a 125 ml single-neck flask fitted with a reflux condenser and equipped with a stir bar. The reaction mixture was heated to reflux temperature under a blanket of nitrogen for 69 hours. Volatiles were removed under reduced pressure. Approximately 2 ml of unreacted starting hydrazide was removed from the product by distillation at 0.133 Pa. The viscous oil which slowly crystallized in the distillation flask was 3-trimethylstannylpropionic acid 2-(2-hydroxycyclohexyl)hydrazide, Compound 99 of Table I. The infrared spectrum (neat) showed the following absorptions: 3280 and 3060 cm$^{-1}$ (—OH and N—H); 1640 and 1530 cm$^{-1}$ (—C=O); 1065 cm$^{-1}$ (C—O); and 760 cm$^{-1}$ (Sn—CH$_3$). The NMR spectrum (CDCl$_3$) showed the following absorptions: a broad doublet centered at 7.52 delta (1H, N—H); a multiplet centered at 4.56 delta (1H, OH); a complex band centered at 3.20 delta (1H, CHO); a triplet centered at 2.38 delta (CH$_2$CO) overlapping a complex band centered at 2.54 delta (CH—N) total intensity of 3 protons; a complex envelope spanning 0.95–2.0 delta (ring CH$_2$) including a triplet centered at 0.99 delta (CH$_2$—Sn) total intensity of 10 protons; and a singlet at 0.06 delta (9H, SnCH$_3$)$_3$) flanked by the J($^{117/119}$Sn—CH$_3$) doublets.

EXAMPLE 12

3'-trimethylstannylpropionic acid 2-(2-hydroxycyclohexyl)-2-(phenylaminocarbonyl)hydrazide 1.36 g (0.011 mole) of phenyl isocyanate was added to a solution of 4.0 g (0.011 mole) of 3'-trimethylstannylpropionic acid 2-(2-hydroxycyclohexyl)hydrazide (Compound 99 of Example 11) in 25 ml of dry tetrahydrofuran under a nitrogen blanket. The reaction was stirred overnight and the solid product was then filtered, and the recrystallization of the solid afforded 2.9 g of 3'-trimethylstannylpropionic acid 2-(2-hydroxycyclohexyl)-2-(phenylaminocarbonyl)hydrazide, Compound 98 of Table I. The infrared spectrum (KBr disc) showed the following absorptions: 3400 cm$^{-1}$, very broad (O—H and N—H); 1660 and 1525 cm$^{-1}$ (C=O); and 750, 520, and 505 cm$^{-1}$ (Sn—CH$_3$). The NMR spectrum (CDCl$_3$) showed the following: broad singlets at 9.96 delta, 9.23 delta, 8.45 delta and 8.26 delta (NH and OH); a complex band centered at 7.25 delta (aromatic protons); broad bands centered at 4.74 delta, 4.55 delta, 4.00 delta and 3.04 delta (OH, CHN and CHO protons of cyclohexane ring); a multiplet centered at 2.57 delta (CH$_2$CO); a complex band with peak maxima at 1.85 delta, 1.65 delta and 1.20 delta (ring CH$_2$); a multiplet centered at 0.98 delta (Sn—CH$_2$); and a singlet at 0.09 delta (Sn(CH$_3$)$_3$) flanked by the J($^{117/119}$Sn—CH$_3$) doublets.

EXAMPLE 13

3'-trimethylstannylpropionic acid 2-[2-(4-t-butylphenylsulfonyl)ethyl]hydrazide

3'-trimethylstannylpropionic acid 2-[1-)4-t-butylphenylsulfonyl)ethyl]hydrazide 2.67 g (0.012 mole) of 4-t-butylphenyl vinyl sulfone was added to a 100 ml single-neck round bottom flask containing a stirred solution of 3.0 g (0.012 mole) of 3-trimethylstannylpropionic acid hydrazide and 50 ml of 95% ethanol. The reaction solution was stirred at room temperature for five days, then heated to 60° C. for 1.5 hours and then refluxed for 2 hours. The solvent was removed at reduced pressure leaving 5.7 g of a viscous oil, a mixture of 60% 3'-trimethylstannylpropionic acid 2-[2-(4-t-butylphenylsulfonyl)ethyl]hydrazide, Compound 149A of Table I and 40% 3'-trimethylstannylpropionic acid 2-[1-(4-t-butylphenylsulfonyl)ethyl]hydrazide, Compound 149B of Table I. The infrared spectrum (neat) showed the following absorptions: 3300 cm$^{-1}$ (N—H); 1660 cm$^{-1}$ (C=O); 1310, 1290 and 1145 cm$^{-1}$ (—SO$_2$—); and 755 cm$^{-1}$ (Sn—CH$_3$). The NMR spectra (CDCl$_3$) of A and B exhibited the following common absorptions: a multiplet centered at 7.87 delta (aromatic protons ortho to t—C$_4$H$_9$); a singlet at 7.51 delta (NH); a triplet centered at 2.34 delta (—CH$_2$CO); a singlet at 1.36 delta (C(CH$_3$)$_3$); and a triplet centered at 0.96 delta (CH$_2$—Sn); Compound A showed the following NMR absorptions: a complex multiplet centered at 3.28 delta (NCH$_2$CH$_2$SO$_2$) and a singlet at 0.05 delta flanked by the J($^{117/119}$Sn—CH$_3$) doublets. Compound B showed the following NMR absorptions: a quartet centeted at 3.70 delta

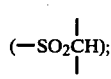
(—SO$_2$CH);

a doublet centered at 1.23 delta

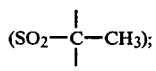
(SO$_2$—C—CH$_3$);

and a singlet at 0.07 delta (Sn(CH$_3$)$_3$)$_2$ flanked by the J($^{117/119}$Sn—CH$_3$) doublets.

EXAMPLE 14

2,6-dimethyl-4-(2'-trimethylstannylethylcarbonylamino)morpholine 36.7 g (0.10 mole) of 3'-trimethylstannylpropionic acid 2,2-bis(2-hydroxypropyl)hydrazide, Compound 140 of Example 9, was heated in a 125 ml flask at 150°-170° C. for one hour. The resultant liquid was then distilled under vacuum to give 30 g of an oily material having a boiling point of 140°-143° C. at 53.2 Pa. Redistillation of the oil under vacuum gave 28 g (80% yield) of a colorless liquid, 2,6-dimethyl-4-(2'-trimethylstannylethylcarbonylamino)morpholine, Compound 145 of Table I. The infrared spectrum (neat) showed the following absorptions: 3350 cm$^{-1}$ (NH); and 1650 cm$^{-1}$

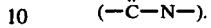
(—C—N—).

The NMR spectrum (CDCl$_3$) showed the following: a broad singlet at 5.13 delta (1H, NH); two broad singlets centered at 4.48 delta and 4.17 delta respectively 1H each, —CH—O); a multiplet centered at 2.72 delta (4H, —NCH$_2$—); a triplet at 2.33 delta

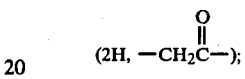
(2H, —CH$_2$C—);

a multiplet centered at 1.23 delta (6H, CH$_3$—C); a triplet at 0.98 delta (2H, CH$_2$Sn—); and a singlet at 0.21 delta (9H, CH$_3$—Sn) flanked by the J($^{117/119}$Sn—CH$_3$) doublets.

EXAMPLE 15

Hexahydro-1,3,5-tris(2-trimethylstannylethylcarbonylamino)-1,3,5-triazine

To a solution of 5.0 g of 3-trimethylstannylpropionic acid hydrazide in 50 ml of 50% aqueous ethanol was added 5.5 g of a 40% aqueous solution of formaldehyde. After stirring for four hours at room temperature, an oily product formed at the bottom of the reaction flask. The solvent was removed under vacuum and the resulting viscous liquid product was distilled under vacuum to give a thick viscous product, hexahydro-1,3,5-tris(2-trimethylstannylethylcarbonylamino)-1,3,5-triazine, having a boiling point of 120°-126° C. at 13.3 Pa, Compound 150 of Table I. Molecular weight measurement by vapor pressure osmometry indicated agreement with the assigned structure. The calculated molecular weight was 788.7 and the measured molecular weight was 777.0. The infrared spectrum (neat) showed the following absorptions: 3100 cm$^{-1}$ (NH); 1650 cm$^{-1}$

(—C—N—).

The NMR spectrum (CDCl$_3$) showed the following: a broad peak at 4.67 delta (1H, NH); a broad singlet at 3.97 delta (2H, NCH$_2$H—); a multiplet centered at 0.97 delta (2H, —CH$_2$Sn—); and a singlet at 0.08 delta (9H, CH$_3$Sn) flanked by the J($^{117/119}$Sn—CH$_3$) doublets.

EXAMPLE 16

3'-trimethylstannylpropionic acid 2,-(3-trimethylstannylpropanoyl)hydrazide

A solid material was recovered from the distillation residue of a several mole preparation of 3-trimethylstannylpropionic acid hydrazide (Compound No. 148 of Example 1). The solid was recrystallized from aqueous ethanol to give 3'-trimethylstannylpropionic acid 2,-(3-trimethylstannylpropanoyl)hydrazide, Compound 97 of Table I. The infrared spectrum (KBr disc) showed the following absorptions: 3220 and 3040 cm$^{-1}$ (N—H); 1685 and 1630 cm$^{-1}$ (C=O); 755 cm$^{-1}$ (CH$_3$—Sn). The NMR spectrum (CDCl$_3$) showed the following: a broadened singlet at 9.24 delta (2H, NH); a multiplet centered at 2.46 delta (4H, CH$_2$C=O); a multiplet centered at 1.0 delta (4H, CH$_2$Sn); and a singlet at 0.08 delta (18H, Sn(CH$_3$)$_3$) flanked by the J($^{117/119}$Sn—CH$_3$) doublets.

EXAMPLE 17

The effectiveness of organotin compounds of the present invention as insecticides was tested according to the following procedures:

A. Mosquito Larvae Test

Formulations were prepared by dissolving 30 mg of organotin compound in 10 ml of acetone. This solution was then diluted to 1 ppm with water. Two 25 ml aliquots were placed in test tubes to which were added 10 to 25 fourth instar larvae of the yellow fever mosquito, *Aedes aegypti* (Linnaeus). The tubes were held in darkness for 72 hours. At the end of this period the percent control was determined. Percent control was calculated using the following equation:

$$\% \text{ Control} = \frac{\text{Number of dead larvea} \times 100}{\text{Total Number of larvea}}$$

B. Aphid Contact Test

Test formulations were prepared for spraying at 1000 ppm concentration by dissolving an organotin compound in a small amount of acetone and adding a suitable wetting agent. Typically, 0.6 gram of organotin compound was dissolved (or suspended) in 10 ml of acetone, 2 drops of Triton-X100 (trademark of Rohm & Haas Co.) wetting agent (octylphenocy polyethoxy ethanol with 9–10 mole percent of polyethylene oxide) were added and this was suspended in 300 ml of water to make a 6000 ppm suspension. An aliquot was then further diluted with distilled water to 1000 ppm concentration of organotin compound.

Eight to ten day old barley seedlings, grown ten plants each in a 12 ounce cup, were infested with corn leaf aphids *Rhopalosiphum maidis* (Fitch), two days prior to treatment. Two pots were treated with each formulation by spraying with a spray atmoizer while the plants were rotating on a turntable. Following treatment, the plants were held for 5 days in the greenhouse. At the end of this period, the percent control of the aphids was estimated based on the reduction of the population density as compared to untreated plants used as controls.

C. Mite One-day Residual Test

Test compounds were prepared as in B, the Aphid Contact Test, but were further diluted to 500 ppm with water.

Cotton, in the second primary leaf stage grown in twelve ounce cups under greenhouse conditions at 21°–24° C., was used in the test.

One plant per pot (two primary leaves) was used for each replicate; two replicates were used for each concentration of organotin compound tested.

The plants were sprayed with the dispersions using a small spray atomizer to thoroughly drench the foliage.

One day following treatment, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves. The percent control was estimated by comparing the number of living mites found with the number found on the control plants.

D. Tobacco Bud Worm Diet Test

Test formulations were prepared at 1000 ppm as in B, the Aphid Contact Test. Two tenths ml of the diluted formulations was pipetted onto the surface of 5 grams of a synthetic diet mixture held in partially filled cells of a plastic jelly tray. Five cells were treated with each chemical dilution. The diet mixture was a modified Vanderzant diet consisting of wheat germ, soyflour, agar, sugar, salts, vitamins, preservatives, and water. The jelly trays had fifty cavities per sheet, each cavity being approximately 2.5×4.0×1.5 cm.

Following treatment, a third or early fourth instar larva of the tobacco bud worm, *Heliothis virescens* (Fabricius), was placed in each cell. The trays were then covered with a plastic film plus a sheet of rigid plastic and were held in an incubator at 27° C.

At the end of one week, the trays were examined and the percent control was determined, adjusted for any natural mortality in the controls by Abbott's formula (See H). The trays were held an additional week and any abnormalities in the development of the survivors was noted.

E. Cotton Boll Weevil Test

Formulations were prepared at 1000 ppm as in B, The Aphid Contact Test. Cotton seedlings 12 to 14 days old grown in 12 ounce cups were used. Two pots were treated with each formulation by spraying with a spray atomizer while rotating the pots on a turntable. Five adult cotton boll weevils, *Anthonomous grandis* Boheman, were placed in each pot following treatment and were caged by covering the pots with an inverted styrofoam cup. Surviving weevils were counted after five days in the greenhouse to determine the percent control, corrected for any natural mortality in the control plants by Abbott's formula.

F. Southern Corn Rootworm Pouch Test

Southern corn rootworm larvae, *Diabrotica undecimpunctata howardi* Barber, were used in the third instar when about one week old.

Chemicals were formulated in water at 100 ppm. 5 ml of a 100 ppm dilution was pipetted onto a double paper towel, inserted into a one quart plastic bag. Bags were held for about 18 hours before being loaded with 5 larvae. Two five-day-old corn seedlings were soaked in the chemical preparation for approximately 1 hour and then placed in the plastic bag. The bags were closed and held at 27° C. for six days. After six days the live larvae were noted and the percent control, adjusted by Abbott's formula, was calculated.

G. Tobacco Budworm One Day Residual Cotton Test

Test formulations were prepared by dissolving 25 mg of organotin compound of the invention in one ml of acetone, adding one drop of Emulphor 719 (trademark of GAF Corp.), a commercial surface-active dispersing agent (polyoxyethylated vegetable oil), and suspended in 50 ml of water for a concentration of 500 ppm (parts per million). Aliquots of the solution were further diluted with distilled water to a concentration of 100 ppm. Pots containing cotton seedlings five weeks old were used. Four plants were treated with each of the diluted formulations applied with a spray atomizer. The following day a third instar larvae of the tobacco budworm, *Heliothis virescens* (Fabricius), was placed on each plant and confined by a cheesecloth net placed over the top.

Percent control of the worms was determined after five days in the greenhouse.

After the sprays were applied, the plants were held in the greenhouse for an additional two weeks, and phytotoxicity observations were then made.

H. Abbott's Formula

Adjusted % mortality =

-continued $$\frac{\% \text{ alive in check} - \% \text{ alive in treated}}{\% \text{ alive in check}} \times 100$$

The results of the above described tests are set forth in Table II below wherein the compound numbers correspond to those in Table I above. As can be seen from the results set forth in Table II, the organotin hydrazide compounds of this invention exhibit good to superior insecticidal activity for a variety of insects.

Table II

| Compound Number | % Control |||||||| 
|---|---|---|---|---|---|---|---|---|
| | Mosquito Larvae 1 PPM | Aphids 1000 PPM | Mites 500 PPM | Tobacco Budworm Diet 1000 PPM | Cotton Boll Weevil 1000 PPM | Southern Corn Rootworm 100 PPM | Tobacco Budworm Cotton 100 PPM | Cotton Phyto at 2 Weeks 100 PPM |
| 1 | 30 | 100 | 100 | 100 | 80 | 68 | 0 | 0 |
| 2 | 0 | 90 | 100 | 100 (2 wks) | 70 | 68 | 64 | 0 |
| 3 | 100 | 40 | 100 | 100 | 90,100 | 100 | 100 | 0 |
| 4 | 100 | 20 | 100 | 100 | 67 | 100 | 100 | 0 |
| 5 | 100 | 0 | 100 | 100 | 56 | 100 | 100 | 0 |
| 6 | 100 | 20 | 100 | 100 | 56 | 0 | 100 | 0 |
| 7 | 100 | 0 | 80 | 100 | 44 | 67 | 100 | 0 |
| 8 | 100 | 50 | 80 | 100 | 71 | 71 | 100 | 0 |
| 9 | 100 | 15 | 75 | 100 | 71 | 100 | 100 | 0 |
| 10 | 100 | 0 | 70 | 100 | 43 | 42 | 100 | 0 |
| 11 | 16 | 40 | 90 | 100 | 57 | 0 | 100 | 0 |
| 12 | 100 | 80 | 95 | 100 | 57 | 71 | 100 | 0 |
| 13 | 100 | 90 | 100 | 100 | 85 | 42 | 100 | 0 |
| 14 | 100 | 60 | 100 | 100 | 85 | 42 | 100 | 0 |
| 15 | 100 | 50 | 90 | 100 | 43 | 0 | 72 | 0 |
| 16 | 100 | 40 | 50 | 100 | 71 | 27 | 100 | 0 |
| 17 | 100 | 100 | 90 | 100 | 80 | 40 | 100 | 0 |
| 18 | 100 | 100 | 90 | 100 | 90 | 80 | 100 | 60 |
| 19 | 100 | 90 | 90 | 100 | 80 | 0 | 100 | 0 |
| 20 | 100 | 100 | 100 | 100 | 80 | 50 | 100 | 3 |
| 21 | 100 | 30 | 40 | 100 | 100 | 0 | 100 | 0 |
| 22 | 7 | 50 | 75 | 100 | 100 | 60 | 100 | 0 |
| 23 | 100 | 0 | 0 | 100 | 100 | 66 | 100 | 0 |
| 24 | 100 | 50 | 40 | 100 | 89 | 0 | 100 | 0 |
| 25 | 91 | 10 | 50 | 100 | 100 | 0 | 100 | 0 |
| 26 | 88 | 80 | 0 | 60 | 100 | 20 | 63 | 0 |
| 27 | 100 | 50 | 90 | 100 | 78 | 20 | 100 | 0 |
| 28 | 100 | 70 | 0 | 100 | 78 | 0 | 100 | 0 |
| 29 | 100 | 50 | 25 | 100 | 67 | 0 | 100 | 6 |
| 30 | 78 | 80 | 100 | 100 | 100 | 58 | 75 | 0 |
| 31 | 100 | 20 | 25 | 100 | 100 | 0 | 100 | 0 |
| 32 | 0 | 30 | 100 | 100 | 100 | 47 | 100 | 0 |
| 33 | 100 | 30 | 100 | 100 | 100 | 16 | 100 | 0 |
| 34 | 100 | 0 | 30 | 100 | 100 | 0 | 100 | 0 |
| 35 | 60 | 0 | 30 | 0 | 100 | 0 | 25 | 0 |
| 36 | 100 | 30 | 100 | 100 | 100 | 20 | 100 | 0 |
| 37 | 75 | 0 | 20 | 0 | 100 | 0 | 0 | 0 |
| 38 | 0 | 0 | 0 | 100 | 33 | 0 | 0 | 0 |
| 39 | 100 | 100 | 100 | 100 | 100 | 100 | 100 | 40 |
| 40 | 100 | 70 | 60 | 100 | 100 | 100 | 100 | 0 |
| 41 | 100 | 90 | 80 | 100 | 80 | 100 | 100 | 0 |
| 42 | 100 | 0 | 50 | 100 | 43 | 0 | 100 | 0 |
| 43 | 0 | 70 | 40 | 100 | 71 | 37 | 100 | 0 |
| 44 | 0 | 60 | 100 | 100 (2 wks) | 40 | 0 | — | — |
| 45 | 0 | 20 | 0 | 0 | 28 | 0 | 0 | 0 |
| 46 | 0 | 30 | 25 | 100 | 67 | 20 | 100 | 0 |
| 47 | 100 | 40 | 25 | 100 | 67 | 20 | 100 | 0 |
| 48 | 40 | 0 | 25 | 100 | 78 | 0 | 100 | 0 |
| 49 | 0 | 20 | 25 | 100 | 67 | 20 | 100 | 0 |
| 50 | 0 | 0 | 90 | 100 | 67 | 0 | 100 | 0 |
| 51 | 0 | 0 | 80 | 100 | 78 | 0 | 100 | 0 |
| 52 | 0 | 40 | 80 | 40 | 40 | 0 | — | — |
| 53 | 100 | 50 | 50 | 100 | 71 | 42 | 50 | 0 |
| 54 | 72 | 0 | 25 | 100 | 43 | 0 | 75 | 0 |
| 55 | 33 | 40 | 25 | 100 | 57 | 0 | 100 | 0 |
| 56 | 100 | 20 | 50 | 100 | 71 | 71 | 50 | 0 |
| 57 | 77 | 30 | 50 | 100 | 43 | 42 | 100 | 0 |
| 58 | 0 | 0 | 50 | 100 | 71 | 42 | 75 | 0 |
| 59 | 100 | 80 | 100 | 100 | 50 | 68 | 100 | 0 |
| 60 | 0 | 100 | 100 | 100 | 50 | 16 | 75 | 6 |
| 61 | 0 | 90 | 100 | 100 (2 wks) | 44 | 60 | 100 | 6 |
| 62 | 0 | 93 | 100 | 100 | 67 | 47 | 100 | 0 |
| 63 | 0 | 100 | 100 | 100 | 85 | 100 | 100 | 0 |
| 64 | 0 | 0 | 90 | 75 | 85 | 100 | 44 | 0 |

Table II-continued

| | | | | % Control | | | | |
|---|---|---|---|---|---|---|---|---|
| Compound Number | Mosquito Larvae 1 PPM | Aphids 1000 PPM | Mites 500 PPM | Tobacco Budworm Diet 1000 PPM | Cotton Boll Weevil 1000 PPM | Southern Corn Rootworm 100 PPM | Tobacco Budworm Cotton 100 PPM | Cotton Phyto at 2 Weeks 100 PPM |
| 65 | 100 | 80 | 100 | 100 | 71 | 100 | 100 | 0 |
| 66 | 42 | 60 | 100 | 100 | 57 | 100 | 100 | 0 |
| 67 | 56 | 50 | 100 | 100 | 57 | 71 | 100 | 0 |
| 68 | 70 | 0 | 75 | 100 | 71 | 71 | 100 | 0 |
| 69 | 0 | 90 | 100 | 100 (2 wks) | 100 | 74 | 100 | 0 |
| 70 | 0 | 90 | 90 | 0 | 100 | 0 | 75 | 20 |
| 71 | 50 | 40 | 0 | 100 (2 wks) | 100 | 0 | 25 | 0 |
| 72 | 0 | 90 | 80 | 100 | 100 | 66 | 75 | 0 |
| 73 | 0 | 90 | 90 | 100 | 100 | 0 | 100 | 20 |
| 74 | 0 | 100 | 90 | 100 | 89 | 0 | 50 | 3 |
| 75 | 100 | 20 | 40 | 100 | 100 | 66 | 75 | 0 |
| 76 | 0 | 50 | 0 | 100 | 100 | 0 | 100 | 0 |
| 77 | 15 | 0 | 0 | 100 | 89 | 0 | 25 | 0 |
| 78 | 40 | 0 | 25 | 100 | 89 | 37 | 100 | 0 |
| 79 | 8 | 0 | 25 | 100 | 100 | 47 | 25 | 0 |
| 80 | 0 | 50 | 50 | 60 | 100 | 40 | 0 | 0 |
| 81 | 0 | 50 | 0 | 100 (2 wks) | 100 | 0 | 25 | 0 |
| 82 | 0 | 30 | 0 | 100 | 67 | 60 | 0 | 0 |
| 83 | 92 | 50 | 0 | 100 | 89 | 20 | 25 | 0 |
| 84 | 100 | 30 | 25 | 100 | 90 | 0 | 50 | 0 |
| 85 | 30 | 30 | 25 | 100 | 90 | 0 | 50 | 0 |
| 86 | 0 | 50 | 95 | 100 | 71 | 71 | 100 | 0 |
| 87 | 0 | 60 | 25 | 100 | 85 | 64 | 100 | 0 |
| 88 | 100 | 0 | 90 | 100 | 78 | 0 | 100 | 0 |
| 89 | 0 | 90 | 50 | 100 (2 wks) | 78 | 20 | 100 | 0 |
| 90 | 100 | 0 | 40 | 100 | 57 | 0 | 100 | 0 |
| 91 | 0 | 0 | 90 | 100 | 71 | 0 | 72 | 0 |
| 92 | 100 | 70 | 60 | 100 | 85 | 42 | 100 | 0 |
| 93 | 0 | 60 | 60 | 100 | 71 | 42 | 50 | 0 |
| 94 | 100 | 10 | 0 | 100 | 89 | 60 | 0 | 0 |
| 95 | 0 | 80 | 80 | 100 | 67 | 100 | 75 | 0 |
| 96 | 0 | 90 | 75 | 50 | 71 | 71 | 0 | 0 |
| 97 | 55 | 40 | 25 | 100 | 90 | 20 | 100 | 0 |
| 98 | 100 | 30 | 0 | 100 | 75 | 0 | 66 | 0 |
| 99 | 80 | 95 | 100 | 40 | 100 | 0 | 50 | 0 |
| 100 | 88 | 100 | 30 | 100 | 50 | — | 100 | 0 |
| 101 | 0 | 0 | 0 | 0 | 70 | 53 | 0 | 0 |
| 102 | 82 | 90 | 75 | 100 (2 wks) | 70 | — | 50 | 0 |
| 103 | 100 | 50 | 25 | 100 (2 wks) | 71 | 0 | 0 | 0 |
| 104 | 34 | 30 | 25 | 100 (2 wks) | 14 | 0 | 33 | 0 |
| 105 | 100 | 25 | 25 | 100 | 89 | 50 | 100 | 0 |
| 106 | 100 | 100 | 60 | 100 | 80 | — | 50 | 0 |
| 107 | 0 | 0 | 0 | 0 | 38 | — | 0 | 0 |
| 108 | 0 | 60 | 90 | 100 (2 wks) | 88 | 100 | 100 | 0 |
| 109 | 100 | 40 | 0 | 100 | 88 | — | 50 | 0 |
| 110 | 0 | 30 | 25 | 0 | 80 | 6 | 0 | 0 |
| 111 | 0 | 97 | 100 | 100 (2 wks) | 90 | — | 100 | 6 |
| 112 | 100 | 40 | 25 | 100 | 100 | — | 75 | 0 |
| 113 | 100 | 40 | 25 | 100 | 40 | 79 | 100 | 0 |
| 114 | 100 | 40 | 25 | 100 | 60 | 50 | 75 | 0 |
| 115 | 100 | 90 | 50 | 100 | 40 | 75 | 25 | 0 |
| 116 | 100 | 70 | 90 | 100 | 60 | 50 | 75 | 0 |
| 117 | 100 | 40 | 25 | 100 (2 wks) | 43 | 0 | 75 | 0 |
| 118 | 100 | 0 | 85 | 100 | 44 | 20 | 100 | 0 |
| 119 | 92 | 30 | 25 | 100 | 60 | 16 | 29 | 0 |
| 120 | 0 | 20 | 0 | 80 (2 wks) | 20 | 53 | — | — |
| 121 | 8 | 20 | 25 | 100 (2 wks) | 80 | 0 | 0 | 0 |
| 122 | 15 | 50 | 50 | 100 (2 wks) | 90 | — | 100 | 0 |
| 123 | 100 | 60 | 25 | 100 | 80 | — | 100 | 0 |
| 124 | 100 | 40 | 30 | 100 | 70 | 0 | 100 | 0 |
| 125 | 58 | 50 | 25 | 100 (2 wks) | 60 | 0 | — | — |
| 126 | 100 | 0 | 25 | 100 | 75 | 14 | — | — |
| 127 | 0 | 40 | 0 | 20 | 30 | — | — | — |
| 128 | 0 | 0 | 0 | 40 | — | 0 | — | — |
| 129 | 0 | 0 | 0 | 60 | — | 0 | — | — |
| 130 | 0 | 60 | 0 | 0 | 22 | 0 | — | — |
| 131 | 0 | 0 | 25 | 12 | 0 | 0 | — | — |
| 132 | 0 | 0 | 0 | 20 | 20 | — | — | — |
| 133 | 0 | 100 | 30 | 100 | 90 | — | 29 | 0 |
| 134 | 0 | 100 | 80 | 40 | 80 | — | 0 | 0 |
| 135 | 0 | 90 | 20 | 80 | 70 | — | 29 | 0 |
| 136 | 0 | 100 | 90 | 100 (2wks) | 90 | — | 29 | 0 |
| 137 | 95 | 40 | 80 | 0 | 60 | 100 | 0 | 0 |
| 138 | 50 | 20 | 25 | 0 | 30 | 0 | 0 | 0 |
| 139 | 6 | 40 | 25 | 40 | 30 | — | — | — |
| 140 | 0 | 100 | 90 | 20 | 80 | — | 0 | 20 |
| 141 | 0 | 100 | 100 | 0 | 60 | 0 | — | — |

Table II-continued

| Compound Number | Mosquito Larvae 1 PPM | Aphids 1000 PPM | Mites 500 PPM | Tobacco Budworm Diet 1000 PPM | Cotton Boll Weevil 1000 PPM | Southern Corn Rootworm 100 PPM | Tobacco Budworm Cotton 100 PPM | Cotton Phyto at 2 Weeks 100 PPM |
|---|---|---|---|---|---|---|---|---|
| 142 | 0 | 90 | 100 | 100 | 88 | 0 | 75 | 6 |
| 143 | 76 | 100 | 96 | 100 (2 wks) | 70 | 18 | 0 | 0 |
| 144 | 15 | 90 | 40 | 0 | 60 | 0 | 0 | 0 |
| 145 | 0 | 100 | 50 | 100 | 100 | — | 0 | 0 |
| 146 | 100 | 60 | 50 | 40 | 40 | — | — | — |
| 147 | 0 | 100 | 100 | 100 (2 wks) | 50 | 79 | 50 | 0 |
| 148 | 0 | 100 | 100 | 100 | 63 | — | 0 | 0 |
| 149 | 100 | 80 | 60 | 100 | 90 | 100 | 100 | 0 |
| 150 | 100 | 90 | 95 | 100 | 80 | 100 | 100 | 0 |

We claim:

1. A compound having the formula $R_3SnACONR^1X$, wherein R is $C_1-C_4$ alkyl, $C_3-C_6$ cycloalkyl, or $C_6-C_{10}$ aryl; A is $C_1-C_5$ alkylene or $C_8$ aralkylene; $R^1$ is hydrogen, $C_1-C_{12}$ alkyl, $C_7-C_9$ aralkyl, $C_2-C_{12}$ alkanoyl, $C_7-C_{11}$ aroyl, or $C_1-C_{12}$ alkyl substituted with hydroxy, cyano, $C_1-C_{14}$ alkoxycarbonyl, $C_1-C_4$ alkylsulfonyl, $C_6-C_{10}$ arylsulfonyl, $C_1-C_4$ alkanoyl, $C_6-C_{10}$ aroyl, or $C_5-C_6$ 2-hydroxycycloalkyl; and X is $-NR^2R^3$, $-N=CR^4R^5$, $-NR^6COR^7$, or $-NR^8CYNR^9R^{10}$, wherein Y is divalent oxygen or sulfur; $R^2$ and $R^3$ may be the same or different and are hydrogen, provided that one of $R^2$ and $R^3$ is other than hydrogen, or are 2-hydroxycyclohexyl, substituted or unsubstituted $C_1-C_{17}$ alkyl, the substituents being the same or different and being hydroxy, $C_6-C_{10}$ aryl, $C_1-C_4$ alkoxy, $C_7-C_{11}$ alkoxyaryloxy, tetrahydropyranyloxy, phenylsulfonylethyl, phenyl substituted with halogen, $C_1-C_{18}$ alkyl, $C_6-C_{10}$ aryl, $C_1-C_4$ alkoxy, or phenoxy, or are $-R^{11}OOCNR^{12}R^{13}$, wherein $R^{11}$ is $C_3-C_6$ cycloalkylene, substituted or unsubstituted $C_2-C_{12}$ alkylene, the substituents being the same or different and being $C_6-C_{10}$ aryl, $C_1-C_4$ alkoxy, $C_7-C_{11}$ alkoxyaryloxy, or tetrahydropyranyloxy; $R^{12}$ is $C_1-C_{18}$ alkyl, $C_3-C_{10}$ cycloalkyl, $C_6-C_{10}$ aryl, or phenyl substituted with halogen or with $C_1-C_8$ alkyl, $C_1-C_4$ alkoxy, $C_2-C_6$ alkoxycarbonyl, trifluoromethyl or $C_1-C_4$ alkylphenylsulfonyl; and $R^{13}$ has the meanings of $R^1$ above; or $R^2$ and $R^3$ are joined together forming $C_4-C_6$ alkylene, $C_4-C_6$ oxydialkylene or methylenebis(aminomethylene)-N,N'-bis(3-trimethylstannyl-ethylcarbonylamino); $R^4$ and $R^5$ may be the same or different and are hydrogen, provided that one of $R^4$ and $R^5$ is other than hydrogen, or are $C_1-C_{11}$ alkyl, $C_3-C_{10}$ cycloalkyl, $C_7-C_{12}$ bicycloalbenyl $C_7-C_{11}$ aralkyl, $C_8-C_{10}$ arylalkenyl, $C_6-C_{10}$ aryl, furyl, pyridyl indolyl, dihydropyranyl, or phenyl substituted with $C_1-C_8$ alkyl, hydroxy, halogen, $C_1-C_8$ alkoxy, methylenedioxy, $C_6-C_{10}$ aryloxy, benzyloxy, $C_2-C_8$ dialkylamino, $C_1-C_8$ alkylamino, $C_6-C_{12}$ arylamino, cyano, or nitro, or $R^4$ and $R^5$ are joined together forming $C_2-C_5$ alkylene; $R^6$, $R^8$ and $R^{10}$ may be the same or different and have the meanings of $R^1$ above; $R^7$ is $C_1-C_{17}$ alkyl, $C_3-C_{10}$ cycloalkyl, $C_6-C_{10}$ aryl, $C_8-C_{10}$ aralkenyl, furyl, phenothiazin-10-yl, trimethylstannylethyl, or phenyl substituted with halogen, $C_1-C_4$ alkyl, $C_6-C_{10}$ aryl, $C_1-C_4$ alkoxy, phenylazo, carboxy, nitro, alkali metal carboxy, or $C_2-C_{12}$ alkoxycarbonyl, or $R^7$ is a pyridylenebis(carbonylamino) group connecting two $R_3SnACONR^1-$ groups, wherein R, A, and $R^1$ are as defined above; $R^9$ is $C_1-C_{18}$ alkyl, $C_3-C_5$ alkenyl, $C_3-C_{10}$ cycloalkyl, $C_6-C_{10}$ aryl, $C_3-C_8$ alkoxycarbonylalkyl, $C_7-C_9$ aralkyl, or phenyl substituted with halogen, $C_1-C_{12}$ alkyl, $C_1-C_4$ alkoxy, nitro, cyano, trifluoromethyl, or alkali metal sulfo.

2. The compound of claim 1, wherein R is $C_1-C_4$ alkyl, cyclohexyl, or phenyl; A is $C_1-C_5$ alkylene; $R^1$, $R^6$, and $R^{10}$ are hydrogen; $R^2$ and $R^3$ may be the same or different and are hydrogen, provided that one of $R^2$ and $R^3$ is other than hydrogen, 2-hydroxycyclohexyl, 4-t-butylphenylsulfonylethyl, substituted or unsubstituted $C_1-C_8$ alkyl, the substituents being the same or different and being phenyl, hydroxy, methoxy, methoxyphenoxy, or tetrahydropyranyloxy, $-R^{11}OOCNR^{12}R^{13}$ wherein $R^{11}$ is cyclohexylene, substituted or unsubstituted $C_1-C_{12}$ alkylene, the substituents being phenyl, methoxy, methoxyphenoxy, or tetrahydropyranyloxy, $R^{12}$ is $C_1-C_{18}$ alkyl, cyclohexyl, phenyl, naphthyl, tolylsulfonyl, or phenyl substituted with halogen, methyl, trifluoromethyl, methoxy, or ethoxycarbonyl, and $R^{13}$ is hydrogen, or $R^2$ and $R^3$ are joined together forming oxybis(isopropylene) or methylenebis(aminomethylene)-N,N'-bis(2-trimethylstannylethylcarbonylamino); $R^4$ and $R^5$ may be the same or different and are hydrogen, provided that one of $R^4$ and $R^5$ is other than hydrogen, or are $C_1-C_{11}$ alkyl, cyclohexyl, norbornenyl, phenyl, naphthyl, dihydropyranyl, furyl, pyridyl, indolyl, or phenyl substituted with halogen, hydroxy, $C_1-C_8$ alkyl, $C_1-C_4$ alkoxy, phenyl, methylenedioxy, phenoxy, benzyloxy, dimethylamino, acetamido, cyano, or nitro, or $R^4$ and $R^5$ are joined together forming pentamethylene; $R^7$ is $C_1-C_{17}$ alkyl, $C_3-C_6$ cycloalkyl, phenyl, styryl, furyl, phenothiazin-10-yl, trimethylstannylethyl, or phenyl substituted with $C_1-C_4$ alkyl, phenyl, methoxy, phenylazo, carboxy, alkali metal carboxy, or nitro, or $R^7$ is a pyridylenebis(carbonylamino) group connecting two $R_3SnACONR^1-$groups, wherein R, A, and $R^1$ are as defined above; $R^8$ is hydrogen or 2-hydroxycyclohexyl; and $R^9$ is $C_1-C_{18}$ alkyl, allyl, cyclohexyl, phenyl, naphthyl, butoxycarbonylmethyl, phenyl substituted with halogen, methyl, trifluoromethyl, methoxy, nitro, or sodiumsulfo.

3. A compound having the formula $R_3Sn_nACONR^1X$, wherein R is methyl; A is ethylene or isopropylene; $R^1$ is hydrogen; and X is $-NR^2R^3$, $-N=CR^4R^5$, $-NR^6COR^7$, or $-NR^8CYNR^9R^{10}$, wherein Y is divalent oxygen or sulfur; $R^2$ and $R^3$ may be the same or different and are hydrogen, provided that one of $R^2$ and $R^3$ is other than hydrogen, 2-hydroxycyclohexyl, 4-t-butylphenylsulfonylethyl, substituted or unsubstituted $C_1-C_8$ alkyl, the substituents being the same or different and being phenyl, hydroxy, methoxy, methoxyphenoxy, or tetrahydropyranyloxy, $-R^{11}OOCNR^{12}R^{13}$ wherein $R^{11}$ is isopropylene, $R^{12}$ is butyl or phenyl and $R^{13}$ is hydrogen, or $R^2$ and $R^3$ are joined together forming oxybis(isopropylene) or methylenebis(aminomethylene)-N,N'-bis(2-trimethylstannylethylcarbonylamino; $R^4$ is hydrogen or benzyl; $R^5$ is phenyl, cyanophenyl or benzyl; $R^6$ and $R^{10}$ are hydrogen; $R^7$ is cyclopropyl; $R^8$ is hydrogen or 2-hydroxycyclohexyl; and $R^9$ is methyl, cyclohexyl, phenyl or methoxyphenyl.

4. 3'-trimethylstannylpropionic acid 2,2-bis[2-methyl-2-(phenylaminocarbonyloxy)ethyl]hydrazide according to claim 3.

5. 3'-trimethylstannylpropionic acid 2,2-bis[2-methyl-2-(2-butylaminocarbonyloxy)ethyl]hydrazide according to claim 3.

6. 3'-trimethylstannylpropionic acid 2-(cyclopropylcarbonyl)hydrazide according to claim 3.

7. 3'-trimethylstannylpropionic acid 2-[(phenylamino)carbonyl]hydrazide according to claim 3.

8. 3'-methyl-3'-trimethylstannylpropionic acid 2-[(phenylamino)carbonyl]hydrazide according to claim 3.

9. 3'-trimethylstannylpropionic acid 2-[(4-methoxyphenylamino)carbonyl]hydrazide according to claim 3.

10. 3'-trimethylstannylpropionic acid 2-[(cyclohexylamino)carbonyl]hydrazide according to claim 3.

11. 3'-trimethylstannylpropionic acid 2-[(methylamino)thioxomethyl]hydrazide according to claim 3.

12. 3-trimethylstannylpropionic acid phenylmethylenehydrazide according to claim 3.

13. 3'-trimethylstannylpropionic acid 4-cyanophenylmethylenehydrazide according to claim 3.

14. 3-methyl-3-trimethylstannylpropionic acid phenylmethylenehydrazide according to claim 3.

15. 3'-trimethylstannylpropionic acid 1,3-diphenyl-2-propylidenehydrazide according to claim 3.

16. A method of controlling insects on plants comprising applying to a plant an insecticidally effective amount of a compound of the formula $R_3SnACONR^1X$, wherein, R, A, $R^1$ and X are as defined in claims 1 or 2.

17. A method according to claim 16, wherein said plant is a cotton plant and said insects are *Heliothis virescens* and *Heliothis zea*.

18. An insect control composition comprising an insecticidally effective amount of a compound of the formula $R_3SnACONR^1X$, wherein R, A, $R^1$ and X are as defined in claim 1 or 2, together with a diluent or carrier.

19. A method of controlling insects on plants comprising applying to a plant an insecticidally effective amount of a compound of the formula $R_3SnACONR^1X$, wherein R, A, $R^1$ and X are as defined in claim 3.

20. A method according to claim 19, wherein said plant is a cotton plant and said insects are *Heliothis virescens* and *Heliothis zea*.

21. An insect control composition comprising an insecticidally effective amount of a compound of the formula $R_3S_nACONR^1X$, wherein R, A, $R^1$ and X are as defined in claim 3, together with a diluent or carrier.

* * * * *

UNITED STATES PATENT AND TRADEMARK OFFICE
CERTIFICATE OF CORRECTION

PATENT NO. : 4,178,382
DATED : December 11, 1979
INVENTOR(S) : Chung-Ling Mao et al.

It is certified that error appears in the above-identified patent and that said Letters Patent are hereby corrected as shown below:

Claim 1, line 46, change "3-trimethylstannyl" to -- 2-trimethylstannyl --

Claim 2, lines 26-27, change "$-R_1^1$" to -- $-R^{11}$ --

Signed and Sealed this

Eighth Day of April 1980

[SEAL]

Attest:

Attesting Officer

SIDNEY A. DIAMOND

Commissioner of Patents and Trademarks